United States Patent
Retboll et al.

(10) Patent No.: US 6,300,515 B1
(45) Date of Patent: Oct. 9, 2001

(54) PROCESS FOR THE ISOMERIZATION OF ALLYLIC COMPOUNDS

(75) Inventors: Mikael Retboll; Yoshinori Hara, both of Kanagawa; Hisao Urata, Ibaraki; Hironobu Ohno, Kanagawa, all of (JP)

(73) Assignee: Mitsubishi Chemical Corporation, Tokyo (JP)

( * ) Notice: Subject to any disclaimer, the term of this patent is extended or adjusted under 35 U.S.C. 154(b) by 0 days.

(21) Appl. No.: 09/550,798

(22) Filed: Apr. 17, 2000

(30) Foreign Application Priority Data

Apr. 15, 1999 (JP) .................................................. 11-107568

(51) Int. Cl.[7] ...................................................... C07C 69/76
(52) U.S. Cl. ..................... 560/113; 560/244; 560/246; 560/262
(58) Field of Search ...................................... 560/113, 262, 560/244, 246

(56) References Cited

U.S. PATENT DOCUMENTS

| | | | |
|---|---|---|---|
| 3,755,423 | 8/1973 | Onoda et al. | 260/497 |
| 3,830,833 | 8/1974 | Mabuchi et al. | 260/491 |
| 4,095,030 * | 6/1978 | Stapp | 560/100 |
| 5,177,254 | 1/1993 | Haji et al. | 560/244 |
| 5,777,155 | 7/1998 | Sato et al. | 560/244 |
| 6,111,134 | 8/2000 | Hara et al. | 560/201 |

FOREIGN PATENT DOCUMENTS

| | | |
|---|---|---|
| 2 134 115 | 1/1972 | (DE) . |
| 24 54 768 | 5/1976 | (DE) . |
| 27 36 695 | 3/1979 | (DE) . |
| 50-126611 | 10/1975 | (JP) . |
| 55011555 * | 1/1980 | (JP) . |
| 55-11555 | 1/1980 | (JP) . |
| 57-140744 | 8/1982 | (JP) . |
| 10212264 * | 8/1998 | (JP) . |
| 2000355572 * | 12/2000 | (JP) . |

OTHER PUBLICATIONS

Bianchi et al. "A new class of oxygen nucleophiles for regioselective 1,4–addition to butadiene monoxide catalyzed by palladium complexes". Tetrahedron Lett. (1997), 38(17), 3081–3084.*

* cited by examiner

Primary Examiner—Ralph Gitomer
(74) Attorney, Agent, or Firm—Oblon, Spivak, McClelland, Maier & Neustadt, P.C.

(57) ABSTRACT

The invention provides a process that includes isomerizing at least one allylic substrate having an acyloxyl group or a hydroxyl group at the allyl position thereof, to produce a corresponding allylic isomer, wherein the isomerizing is conducted in the presence of a catalyst that includes a Group VIII-X metal compound and a phosphite compound. The invention also provides a process that includes: (1) diacetoxylating butadiene to obtain a mixture containing at least one selected from the group including 3,4-diacetoxy-1-butene, 3-butene-1,2-diolmonoacetoxylate and a mixture thereof, and at least one selected from the group including 4-diacetoxy-2-butene, acetoxy-4-hydroxy-2-butene and a mixture thereof; (2) separating, from the mixture, a portion containing at least one selected from the group including the 3,4-diacetoxy-1-butene, the 3-butene-1,2-diolmonoacetoxylate, and a mixture thereof; (3) isomerizing at least a part of the portion in the presence of a catalyst, to obtain an isomerization product mixture; (4) optionally, recirculating at least a part of the isomerization product mixture to at least one selected from the group including the isomerizing, the separating, the mixture, and combinations thereof. The processes of the present invention achieve both high conversion rates and high selectivity, and suppress the otherwise undesirable deposition of metals.

67 Claims, 2 Drawing Sheets

PROCESS FOR THE ISOMERIZATION OF ALLYLIC COMPOUNDS

BACKGROUND OF THE INVENTION

1. Field of the Invention

The present invention relates to a process for isomerizing a compound having an acyloxyl group or a hydroxyl group at the allylic position thereof. The present invention also relates to a process for isomerizing 3,4-disubstituted-1-butene and/or 1,4-disubstituted-2-butene using a specific catalyst to produce, respectively, the corresponding isomers, 1,4-disubstituted-2-butene and/or 3,4-disubstituted-1-butene.

2. Discussion of the Background 1,4-diacetoxy-2-butene is an important intermediate for producing 1,4-butanediol, tetrahydrofuran or the like. 3,4-diacetoxy-1-butene is an important intermediate for producing medicines, agricultural chemicals, various aromatics, terpentene compounds such as vitamin A acetate, and the like.

It is known that 1,4-diacetoxy-2-butene and 3,4-diacetoxy-1-butene may be obtained by oxidizing butadiene in an acetic acid solvent with molecular oxygen (e.g., Laid-Open Japanese Patent Application (JP-A) Nos. 48-72090, 48-96513). However, it is extremely difficult to produce 1,4-diacetoxy-2-butene and 3,4-diacetoxy-1-butene in an arbitrary ratio by this method, since the production ratio of 1,4-diacetoxy-2-butene to 3,4-diacetoxy-1-butene is influenced mainly by the ability of the catalyst.

Although 3,4-diacetoxy-1-butene is easily obtained by acetoxylating 1,2-epoxy-3-butene, it is extremely difficult to obtain 1,4-diacetoxy-2-butene by this method. On the other hand, extremely specific raw materials such as 3,6-dihydro-1,2-dioxine and the like are required for producing only 1,4-diacetoxy-2-butene selectively. Therefore, it is virtually impossible to produce 1,4-diacetoxy-2-butene on an industrial scale.

Accordingly, conventional methods for isomerizing 3,4-disubstituted-1-butene and/or 1,4-disubstituted-2-butene using a particular catalyst have been suggested to produce the corresponding respective isomers, 1,4-diacetoxy-2-butene and/or 3,4-diacetoxy-1-butene. These include, for example, a method using a platinum chloride compound as a catalyst (DE U.S. Pat. Nos. 2,736,695 and 2,134,115), a method using a palladium compound in combination with hydrogen chloride or hydrogen bromide (JP-A No. 57-140744), a method using a $PdCl_2(PhCN)_2$ compound (U.S. Pat. No. 4,095,030) and the like. However, these methods use a halogen compound as a catalyst and have problems with the stability of the catalyst. These methods are undesirable industrially since they require large amounts of corrosive halogen compound.

Methods are known which avoid the use of halogen compounds, and these include a method using a catalyst composed of a palladium compound and an organic phosphine (JP-A No. 55-11555) and a method of conducting isomerization in a gas phase using an acid catalyst such as alumina, zeolite and the like (DE-Patent No. 3326668, JP-A No. 50-126611). However, these methods have problems in that either the activity of the catalyst is unsatisfactory or the selectivity of the catalyst is not sufficient and the like, and, accordingly, these methods are unsatisfactory from an industrial point of view.

As described above, 1,4-diacetoxy-2-butene and 3,4-diacetoxy-1-butene are intermediates for utterly different product groups, as noted above. Since each intermediate is useful in widely varying applications, the desired ratio, e.g., in a mixture of 1,4-diacetoxy-2-butene and 3,4-diacetoxy-1-butene depends greatly on area, era or business background of an enterprise carrying them out. Namely, it is extremely significant to isomerize 3,4-diacetoxy-1-butene and/or 1,4-diacetoxy-2-butene to produce the corresponding respective isomers, ,4-diacetoxy-2-butene and/or 3,4-diacetoxy-1-butene, according to industrial needs.

SUMMARY OF THE INVENTION

Accordingly, one object of the present invention is to provide a process for isomerizing allylic substrates having at the allyl position an acyloxyl group or a hydroxyl group to produce the respective corresponding allylic isomers and which avoids the aforementioned problems.

Another object of the present invention is to provide a process for isomerizing allylic substrates having at the allyl position an acyloxyl group or a hydroxyl group, such as 3,4-disubstituted-1-butene and/or 1,4-disubstituted-2-butene and the like.

Another object of the present invention is to provide a process for isomerizing allylic substrates having at the allyl position an acyloxyl group or a hydroxyl group, such as 3,4-disubstituted-1-butene and/or 1,4-disubstituted-2-butene and the like, to produce allylic compounds such as 1,4-disubstituted-2-butene and/or 3,4-disubstituted-1-butene and the like.

Another object of the present invention is to provide a process for isomerizing allylic substrates having at the allyl position an acyloxyl group or a hydroxyl group at a high conversion rate.

Another object of the present invention is to provide a process for isomerizing allylic substrates having at the allyl position an acyloxyl group or a hydroxyl group with high selectivity.

Another object of the present invention is to provide a process for isomerizing allylic substrates having at the allyl position an acyloxyl group or a hydroxyl group while suppressing the deposition of metals derived from isomerization catalyst compounds.

Another object of the present invention is to provide a process that contributes to the efficient production of 1,4-butylene glycol.

These and other objects have been achieved by the present invention, the several embodiments of which are summarized below.

Accordingly, one embodiment of the invention provides a process, that includes:

isomerizing at least one allylic substrate having an acyloxyl group or a hydroxyl group at the allyl position thereof, to produce a corresponding allylic isomer, wherein the isomerizing is conducted in the presence of a catalyst that includes a Group VIII-X metal compound and a phosphite compound.

Another embodiment of the present invention provides a process for isomerizing a mixture of 3,4-diacetoxy-1-butene and 1,4-diacetoxy-2-butene to produce a mixture of the corresponding allylic isomers, 1,4-diacetoxy-2-butene and 3,4-diacetoxy-1-butene, wherein the isomerization is conducted in the presence of a catalyst containing a Group VIII-X metal compound and a phosphite compound.

Another embodiment of the present invention provides a process for isomerizing 3,4-diacetoxy-1-butene to produce the corresponding allylic isomer, 1,4-diacetoxy-2-butene, wherein the isomerization is conducted in the presence of a catalyst containing a Group VIII-X metal compound and a phosphite compound.

Another embodiment of the present invention provides a process for isomerizing 1,4-diacetoxy-2-butene to produce the corresponding allylic isomer, 3,4-diacetoxy-1-butene, wherein the isomerization is conducted in the presence of a catalyst containing a Group VIII-X metal compound and a phosphite compound.

Another embodiment of the invention provides a process for isomerizing a mixture of 3,4-diacetoxy-1-butene and 3-butene-1,2-diolmonoacetoxylate to produce a mixture of the corresponding allylic isomers, 1,4-diacetoxy-2-butene and 1-acetoxy-4-hydroxy-2-butene, wherein the isomerization is conducted in the presence of a catalyst containing a Group VIII-X metal compound and a phosphite compound.

Another embodiment of the invention provides a process for isomerizing a mixture of 3,4-disubstituted-1-butene and 3-butene-1,2-diolmonosubstituted to produce a mixture of the corresponding allylic isomers, 1,4-disubstituted-2-butene and 1-monosubstituted-4-hydroxy-2-butene, wherein the isomerization is conducted in the presence of a catalyst containing a Group VIII-X metal compound and a phosphite compound.

Another embodiment of the invention provides a process, that includes:

(1) diacetoxylating butadiene to obtain a mixture containing at least one selected from the group including 3,4-diacetoxy-1-butene, 3-butene-1,2-diolmonoacetoxylate and a mixture thereof, and at least one selected from the group including 4-diacetoxy-2-butene, acetoxy-4-hydroxy-2-butene and a mixture thereof;

(2) separating, from the mixture, a portion containing at least one selected from the group including the 3,4-diacetoxy-1-butene, the 3-butene-1,2-diolmonoacetoxylate, and a mixture thereof;

(3) isomerizing at least a part of the portion in the presence of a catalyst, to obtain an isomerization product mixture;

(4) optionally, recirculating at least a part of the isomerization product mixture to at least one selected from the group including the isomerizing, the separating, the mixture, and combinations thereof.

By means of the process of the present invention, it is possible to obtain the corresponding allylic isomers at high conversion rates and at high selectivity while suppressing the deposition of metals.

DETAILED DESCRIPTION OF THE INVENTION

Figure 1:
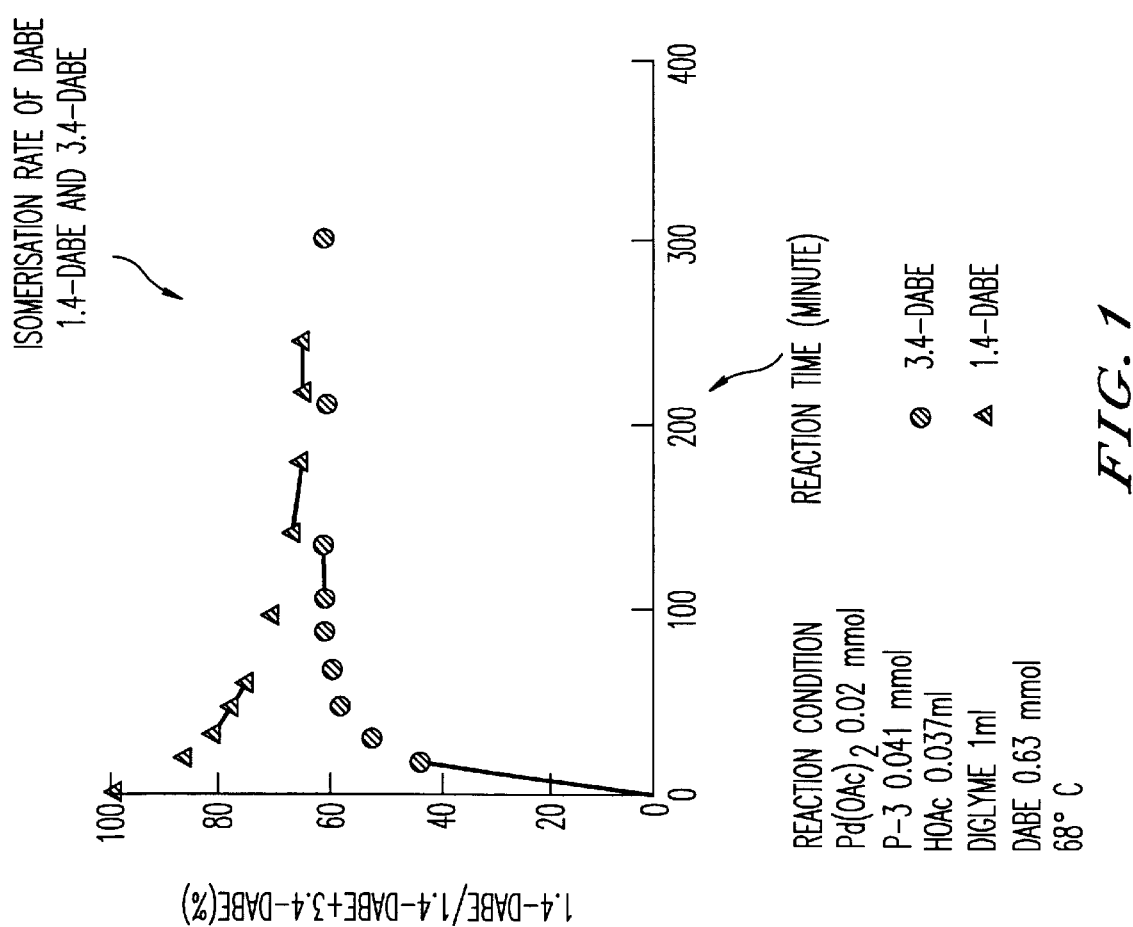
FIG. 1 is a view showing isomerization time conversions of 3,4-diacetoxy-1-butene and 1,4-diacetoxy-2-butene, respectively.
Figure 2:
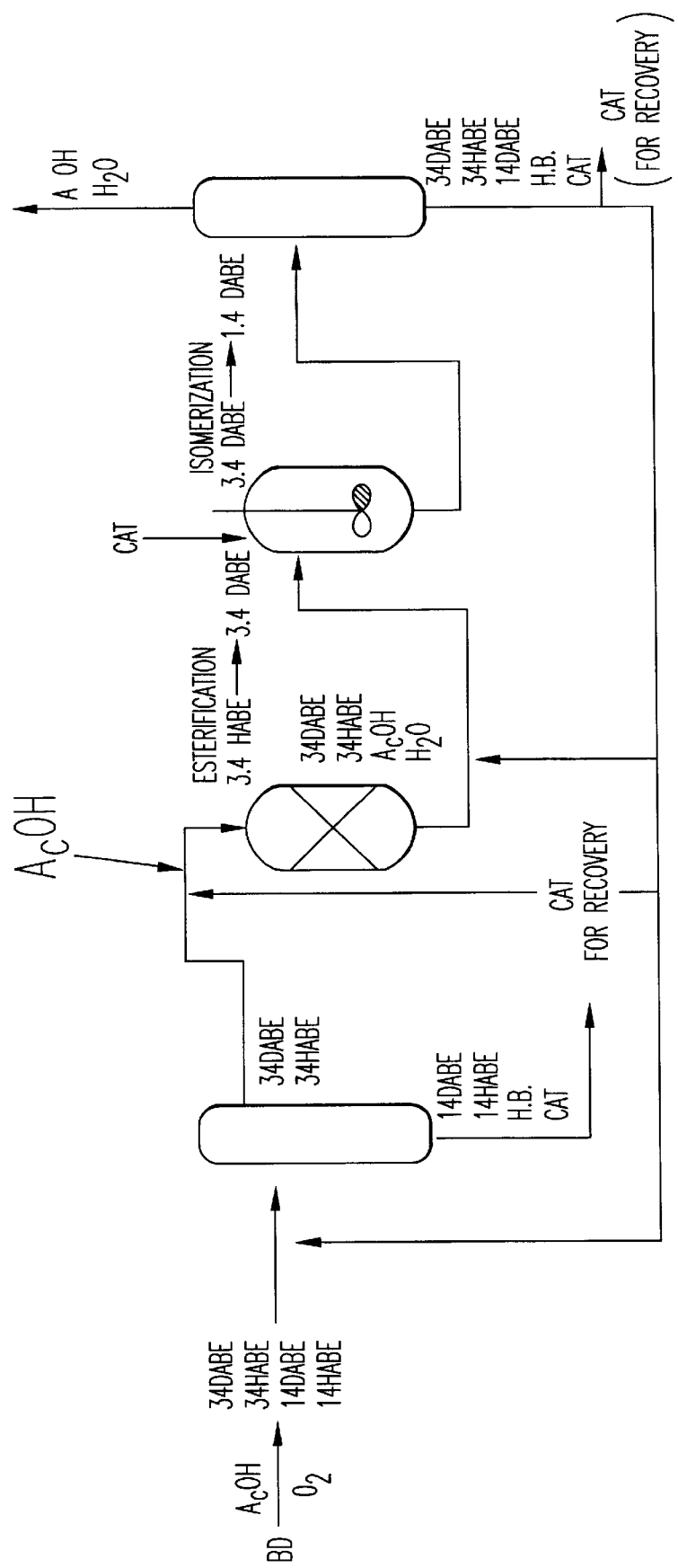
FIG. 2 is a view showing a preferred embodiment of the invention.

Various other objects, features and attendant advantages of the present invention will be more fully appreciated as the same becomes better understood from the following detailed description of the preferred embodiments of the invention.

The raw materials used in the isomerization of the present invention may be any allylic substrate having at the allyl position an acyloxyl or a hydroxyl group, and the present invention includes a process for causing allyl rearrangement of these raw materials to produce the corresponding allylic isomers. Preferably, in the present invention, allylic substrates represented by the following formulae (a) and/or (b) can be isomerized to produce the corresponding allylic isomers of the formulae (b) and/or (a).

Formula (a)

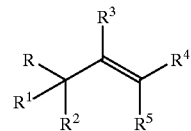

Formula (b)

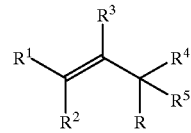

In the above-described formulae (a) and (b), R represents an acyloxyl group (which is usually represented by the formula, $R_A C(O)O$—, wherein $R_A$ is preferably a $C_{1-10}$ alkyl group or a $C_{6-15}$ aryl group, and more preferably a $C_{1-3}$ alkyl group, and most preferably a methyl group) or a hydroxyl group; each substituent $R^1$ through $R^5$, independent of one another, represents a hydrogen atom, a hydroxyl group, a halogen atom, a cyano group, optionally substituted $C_1$–$C_{20}$ alkyl, optionally substituted $C_1$–$C_{20}$ alkoxy, optionally substituted $C_3$–$C_{20}$ cycloalkyl, optionally substituted di-$C_1$–$C_{20}$ alkylamino, optionally substituted $C_6$–$C_{20}$ aryl, optionally substituted $C_6$–$C_{20}$ aryloxy, optionally substituted $C_6$–$C_{20}$ alkylaryl, optionally substituted $C_6$–$C_{20}$ alkylaryloxy, optionally substituted $C_6$–$C_{20}$ arylalkoxy group, optionally substituted $C_2$–$C_{20}$ ester and the like. In each of the above optionally substituted groups, the substituent may include at least one $C_1$–$C_{10}$ alkoxy group, $C_1$–$C_{10}$ carboxyl group, hydroxyl group, $C_6$–$C_{10}$ aryl group and the like and also combinations thereof. For each of the above groups and substituents, the carbon ranges include $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, and $C_{20}$, as appropriate.

In the above-described formula (a), 3,4-disubstituted-1-butene of the formula (a'): $CH_2$=CH—$CHR^6$—$CH_2R^7$ (wherein, $R^6$ and $R^7$ are each independently an acyloxyl group or a hydroxyl group) is preferred, and in the above-described formula (b), 1,4-disubstituted-2-butene of the formula (b'): $CH_2R^8$—CH=CH—$CH_2R^9$ (wherein, $R^8$ and $R^9$ are each independently an acyloxyl group or a hydroxyl group) is preferred.

As the 3,4-disubstituted-1-butene of the formula (a'), 3,4-diacetoxy-1-butene, 3-butene-1,2-diol monoacetoxylates and 3,4-dihydroxybutene-1 are more preferred, and as the 1,4-disubstituted-2-butene of the formula (b'), 1,4-diacetoxy-2-butene, 1-acetoxy-4-hydroxy-2-butene and 1,4-dihydroxybutene-2 are more preferred.

Preferred examples of raw materials for the isomerization reaction can be obtained according to any known method for producing 3,4-diacetoxy-1-butene. For example, 3,4-diacetoxy-1-butene is a by-product in the production of 1,4-diacetoxy-2-butene by reacting butadiene with acetic acid and oxygen in the presence of a catalyst such as palladium and the like, and can be produced according to Japanese Patent Application Publications (JP-B) No. 51-23008 or 59-28553, for example.

The raw material may be a pure material or also be a mixture of a plurality of allylic substrates, and further, other components which do not disturb this isomerization reaction. For example, acetic acid, water and the like may also be contained in the mixture other than the raw materials, and allylic substrates.

The isomerization catalyst used in the reaction of the present invention is a catalyst containing a Group VIII through X (IUPAC Inorganic Chemical Nomenclature revised edition (1989)) metal compound and a phosphite compound. Preferable examples of the metal compound include one or more compounds selected from the compounds of iron, cobalt, nickel, ruthenium, rhodium, platinum, iridium, osmium and palladium, and of them, nickel, palladium and platinum compounds are more preferable. Palladium and platinum compounds are most preferred, and a palladium compound is most particularly preferable. Mixtures may also be used.

Preferred examples of the above-described metal compound include inorganic salts and organic salts, and more preferably, acetic acid salts, acetyl acetonate, halides, sulfate salts, nitrate salts, alkene compounds, amine compound, pyridine compound, phosphine coordinated compounds, phosphite coordinated compounds and the like. Mixtures may also be used.

As the ruthenium compound, $RuCl_3$, $Ru(OAc)_3$, $Ru(acac)_3$, $RuCl_2(PPh_3)_3$ and the like are preferred; as the osmium compound, $OsCl_3$, $Os(OAc)_3$ and the like are preferred, and as the rhodium compound, $RhCl_3$, $Rh(OAc)_3$, rhodium diacetate dimer, $Rh(acac)(CO)_2$, $\{Rh(OAc)(COD)\}_2$, $\{RhCl(COD)\}_2$, $Rh(COD)OAc$ and the like are preferred.

As the iridium compound, $IrCl_3$, $Ir(OAc)_3$ and the like are preferred, and as the nickel compound, $NiCl_2$, $NiBr_2$, $Ni(NO_3)_2$, $NiSO_4$, $Ni(COD)_2$, $NiCl_2(PPh_3)_2$ and the like are preferred.

Preferred examples of the palladium compound include $Pd(0)$ and $PdCl_2$, $PdBr_2$, $PdCl_2(COD)$, $PdCl_2(PPh_3)_2$, $Pd(PPh_3)_4$, $Pd_2(dba)_3CHCl_3$, $K_2PdCl_4$, $K_2PdCl_6$ (potassium hexachloropalladate (IV), $PdCl_2(PhCN)_2$, $PdCl_2(CH_3CN)_2$, $Pd(dba)_2$, $Pd_2(dba)_3$, $Pd(NO_3)_2$, $Pd(OAc)_2$, $Pd(CF_3COO)_2$, $PdSO_4$, $Pd(acac)_2$, carboxylate compounds, olefin-containing compounds, organic phosphine-containing compounds such as $Pd(PPh_3)_4$ and the like, allylpalladium chloride dimer and the like. Carboxylate compounds or halides of palladium such as $Pd(OAc)_2$, $PdCl_2$ and the like are more preferable.

As the platinum compound, $Pt(acac)_2$, $PtCl_2(COD)$, $PtCl_2(CH_3CN)_2$, $PtCl_2(PhCN)_2$, $Pt(PPh_3)_4$, $K_2PtCl_4$, $Na_2PtCl_6$, $H_2PtCl_6$ and the like are preferred (wherein, COD: cyclopentadiene; dba: dibenzylidene acetone; and acac: acetyl acetonate).

In the present invention, the form of the above-described metal compound is not particularly restricted, and active metal complex species may be monomers, dimers and/or multimers.

The amount of the metal compounds is not particularly restricted, and is preferably present in the isomerization reaction system within a range of $1 \times 10^{-8}$ (0.1 mol ppm) to 0.01 mol equivalent, more preferably of $1 \times 10^{-7}$ to 0.001 mol equivalent, and particularly preferably of $1 \times 10^{-6}$ to 0.0001 mol equivalent, based on the total moles of allylic substrates, from the standpoints of catalyst activity and economy of the process.

The phosphite compound used in the present invention is not particularly restricted, and the preferred phosphite compounds are at least one of the compounds of the following general formulae (I), (II), (III), (IV), (V) and (VI).

(I)

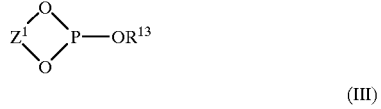

(II)

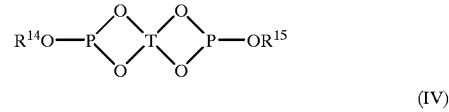

(III)

$(R^{16}O)(R^{17}O)P-O-A^1-O-P(OR^{18})(OR^{19})$ (IV)

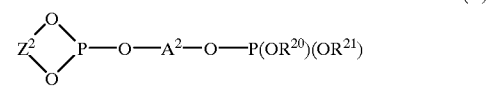

(V)

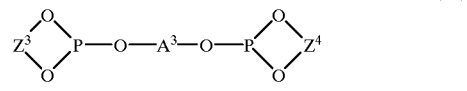

(VI)

In the formulae (I) through (VI), each $R^{10}$ through $R^{21}$ independently of one another represents an alkyl, alkoxy, cycloalkyl, aryloxy, alkylaryloxy, or arylalkoxy group, or an aryl group, each group optionally having one or more substituents.

Regarding the aforementioned alkyl group and the alkyl portion of the aforementioned groups (e.g., the alkyl in alkylaryloxy, hereinafter the "alkyl partial group") of $R^{10}$ through $R^{21}$, the number of carbon atoms therein is preferably from 1 to 20, and more preferably from 1 to 14. Preferred examples of the aforementioned alkyl group and alkyl partial groups include a methyl group, ethyl group, n-propyl group, i-propyl group, n-butyl group, i-butyl group, sec-butyl group, t-butyl group, hexyl group, octyl group, decyl group and the like. The alkyl group or alkyl partial group of $R^{10}$–$R^{21}$ may have one or more substituents, which may include one or more cyano groups, hydroxyl groups, halogen atoms, $C_1$–$C_{10}$ alkoxy groups, $C_6$–$C_{10}$ aryl groups, amino groups, and $C_2$–$C_{10}$ ester groups, and combinations thereof.

Regarding the aforementioned aryl group and also the aryl partial groups in $R^{10}$–$R^{21}$, the number of carbon atoms therein is preferably from 6 to 20, and more preferably from 6 to 14. Most preferred examples of the aforementioned aryl group and aryl partial groups include a phenyl group, tolyl group, xylyl group, di-t-butylphenyl group, naphthyl group, di-t-butylnaphthyl group and the like. The aryl group or aryl partial group of $R^{10}$–$R^{21}$ may have one or more substituents, which may be a hydrogen atom, a cyano group, a hydroxyl group, a halogen atom, a $C_1$–$C_{20}$ alkyl, alkoxy, $C_3$–$C_{20}$ cycloalkyl, $C_6$–$C_{20}$ aryl, $C_6$–$C_{20}$ aryloxy, $C_6$–$C_{20}$ alkylaryl, $C_6$–$C_{20}$ alkylaryloxy, $C_6$–$C_{20}$ arylalkyl, $C_6$–$C_{20}$ arylalkoxy group, or a $C_2$–$C_{20}$ ester group.

Other, more preferred examples of $R^{10}$ through $R^{21}$ include a phenyl group, 2-methylphenyl group, 3-methylphenyl group, 4-methylphenyl group, 2,3-dimethylphenyl group, 2,4-dimethylphenyl group, 2,5-dimethylphenyl group, 2,6-dimethylphenyl group, 2-ethylphenyl group, 2-isopropylphenyl group, 2-t- butylphenyl group, 2,4-di-t-butylphenyl group, 2-chlorophenyl group, 3-chlorophenyl group, 4-chlorophenyl group, 2,3-dichlorophenyl group, 2,4-dichlorophenyl group, 2,5-dichlorophenyl group, 3,4-dichlorophenyl group, 3,5-dichlorophenyl group, 4-trifluoromethylphenyl group, 2-methoxyphenyl group, 3-methoxyphenyl group, 4-methoxyphenyl group, 3,5-dimethoxyphenyl group, 4-cyanophenyl group, 4-nitrophenyl group, trifluoromethyl group, pentafluoroethyl group, pentafluorophenyl group, and the following (C-1) through (C-8).

(C-1)

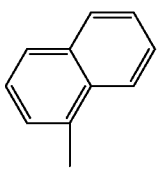
(C-2)

(C-3)

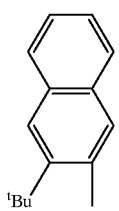
(C-4)

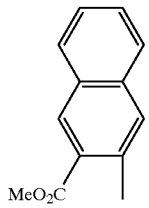
(C-5)

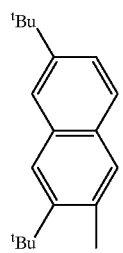
(C-6)

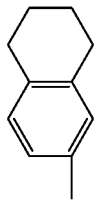
(C-7)

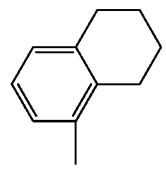
(C-8)

Each $Z^1$, $Z^2$, $Z^3$, $Z^4$, $A^1$, $A^2$ and $A^3$, which are independent of one another, represents a $C_1$–$C_{20}$ alkylene group optionally having one or more substituents, a $C_6$–$C_{30}$ arylene group optionally having one or more substituents or a $C_{12}$–$C_{40}$ diarylene group, —$Ar^1$—$(Q^1)_n$—$Ar^2$— (wherein, each $Ar^1$ and $Ar^2$, which are independent of one another, represents a $C_6$–$C_{18}$ arylene group optionally having one or more substituents).

T represents a carbon atom, alkanetetrayl or benzenetetrayl group or a tetravalent group of $T^1$—$(Q^2)_n$—$T^2$ optionally having one or more substituents, wherein each $T^1$ and $T^2$, which are independent of one another, represents the same or different trivalent organic group (preferably $C_1$–$C_{10}$ alkanetriyl or $C_6$–$C_{15}$ benzenetriyl group), which may each independently have one or more substituents.

Each $Q^1$ and $Q^2$, which are independent of one another, represents —$CR^{22}R^{23}$—, —O—, —S— or —CO—, and each $R^{22}$ and $R^{23}$, which are independent of one another, represents a hydrogen atom, $C_1$–$C_{10}$ alkyl or $C_6$–$C_{10}$ aryl group, each optionally having one or more substituents, and n is 0 or 1.

When any of $Z^1$–$Z^4$ or $A^1$–$A^3$ represents an alkylene group, preferred examples of the alkylene group include a tetramethylethylene group, dimethylpropylene group and the like, and when any of $Z^1$–$Z^4$ or $A^1$–$A^3$ represents an alkylene group optionally having one or more substituents, preferred examples of the substituent include amino groups, cyano groups, hydroxy groups, amide groups, nitro groups, trifluoromethyl groups, trimethylsilyl groups, halogen atoms, $C_1$–$C_{10}$ alkoxy groups, $C_6$–$C_{10}$ aryl groups, and $C_2$–$C_{10}$ ester groups. Combinations of substituents are possible.

When any of $Z^1$–$Z^4$ or $A^1$–$A^3$ represents an arylene group, preferred examples of the arylene group include a phenylene group, naphthylene group and the like. The arylene group may have one or more substitutents, and preferable examples of the substituent include $C_1$–$C_8$ alkyl groups, $C_1$–$C_{10}$ alkoxy groups, $C_6$–$C_{10}$ aryl groups, amino groups, cyano groups, amide groups, nitro groups, trifluoromethyl groups, trimethylsilyl groups, $C_2$–$C_{10}$ ester groups, hydroxyl groups, halogen atoms and the like. Combinations of substituents are possible.

When any of $Z^1$–$Z^4$ or $A^1$–$A^3$ represents a diarylene group, —$Ar^1$—$(Q^1)_n$—$Ar^2$—, $Ar^1$ and $Ar^2$ may each independently represent an arylene group optionally having one or more substituents, and the preferable number of carbon atoms the arylene group is from 6 to 24, more preferably from 6 to 16; and preferable examples of the substituent include cyano group, hydroxyl groups, halogen atoms, $C_1$–$C_{10}$ alkyl groups, $C_1$–$C_{10}$ alkoxy groups, $C_6$–$C_{10}$ aryl groups, amino groups, $C_2$–$C_{10}$ ester groups and the like. Combinations of substituents are possible.

Preferred examples of $A^1$–$A^3$ include —$(CH_2)_2$—, —$(CH_2)_3$—, —$(CH_2)_4$—, —$(CH_2)_5$—, —$(CH_2)_6$—, —CH($CH_3$)—CH($CH_3$)—, —CH($CH_3$)$CH_2$CH($CH_3$)—, —C($CH_3$)$_2$—C($CH_3$)$_2$—, —C($CH_3$)$_2$—$CH_2$—C($CH_3$)$_2$—, and the following (A-1) through (A-47).

Preferred examples of $Z^1$–$Z^4$ include —$(CH_2)_2$—, —$(CH_2)_3$—, —$(CH_2)_4$—, —$(CH_2)_5$—, —$(CH_2)_6$—, —CH($CH_3$)—CH($CH_3$)—, —CH($CH_3$)$CH_2$CH($CH_3$)—, —C($CH_3$)$_2$—C($CH_3$)$_2$—, —C($CH_3$)$_2$—$CH_2$—C($CH_3$)$_2$—, and the following (A-1) through (A-46).

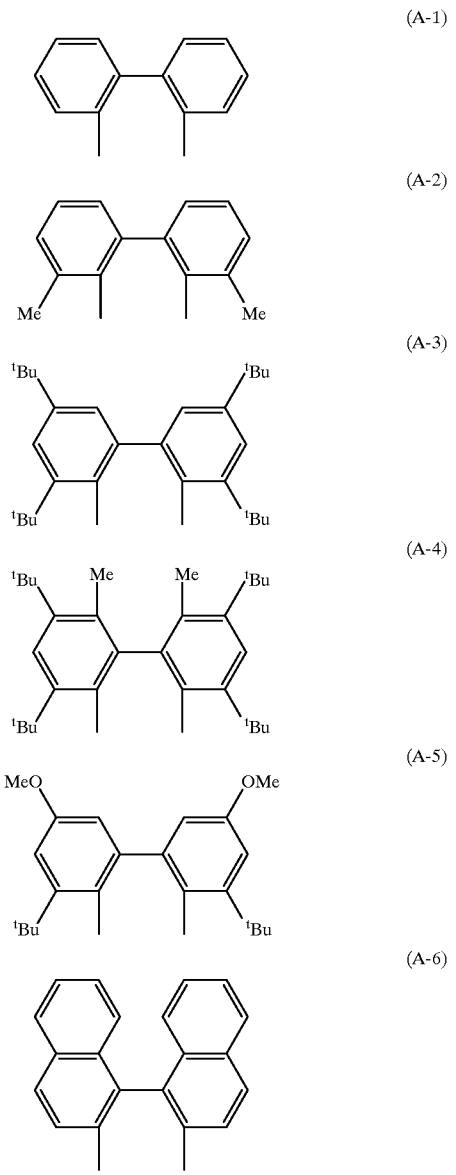

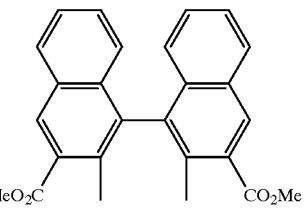

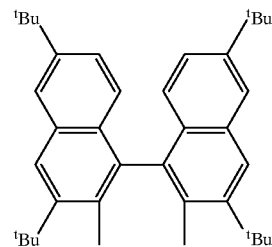

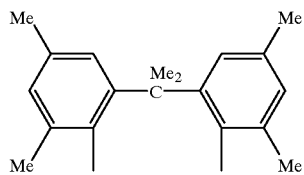

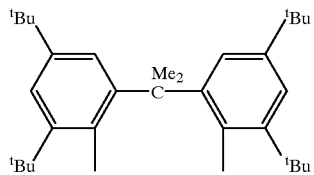

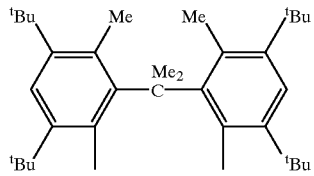

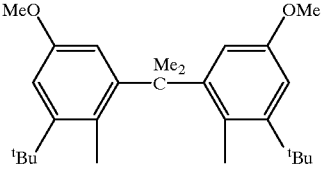

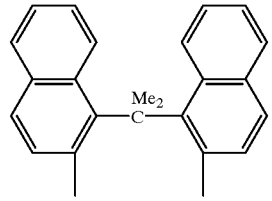

(A-14)
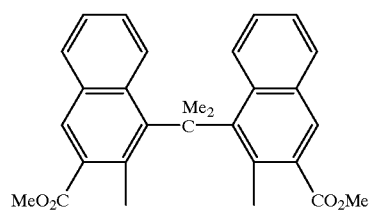
(A-15)
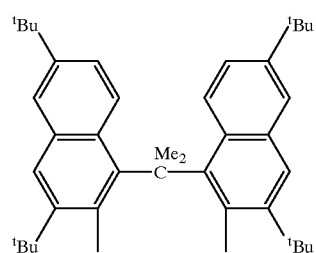
(A-16)
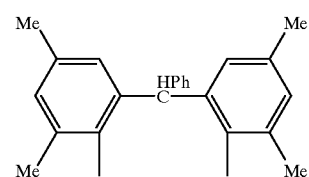
(A-17)
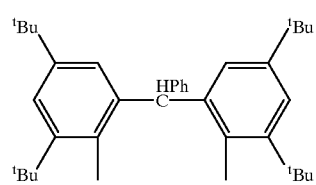
(A-18)
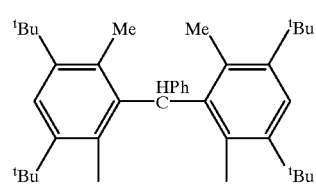
(A-19)
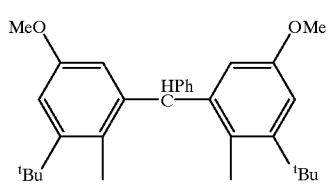
(A-20)
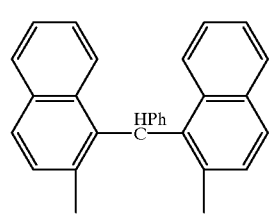
(A-21)
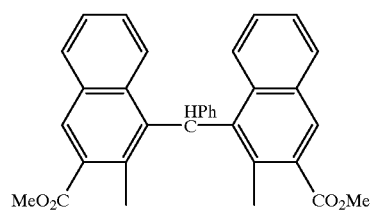
(A-22)
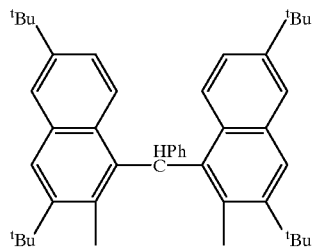
(A-23)
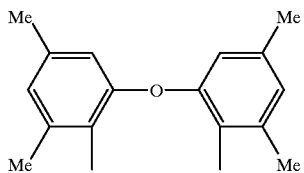
(A-24)
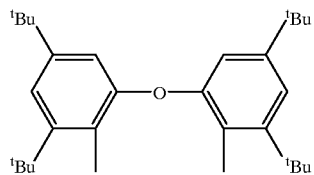
(A-25)
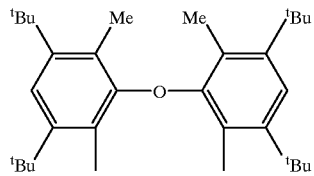
(A-26)
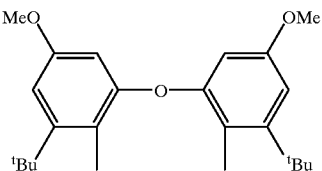
(A-27)
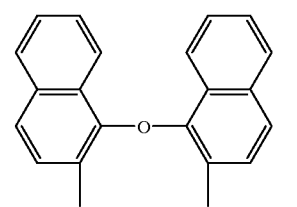

(A-28) 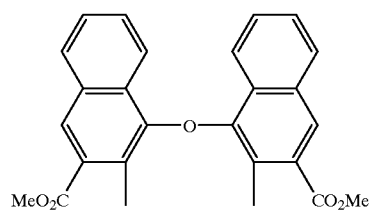
(A-29) 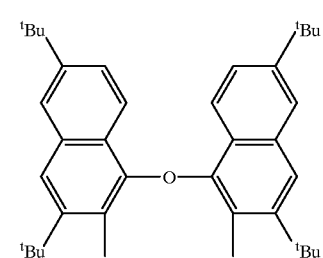
(A-30) 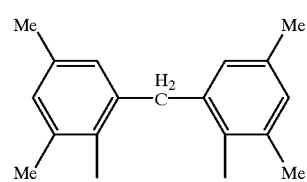
(A-31) 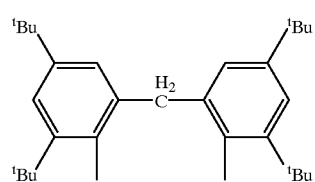
(A-32) 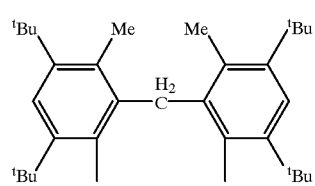
(A-33) 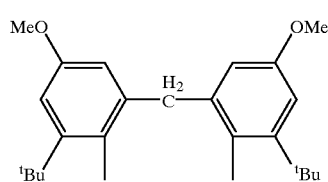
(A-34) 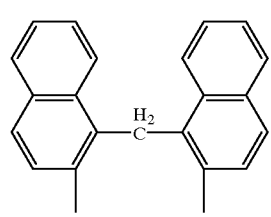
(A-35) 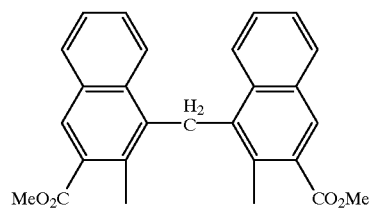
(A-36) 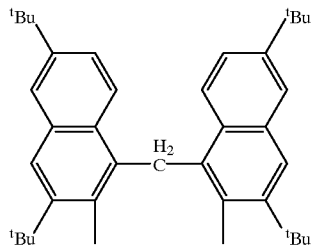
(A-37) 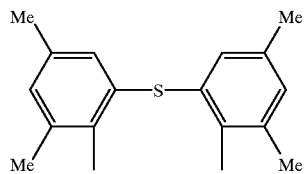
(A-38) 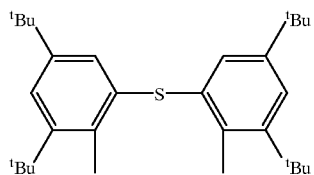
(A-39) 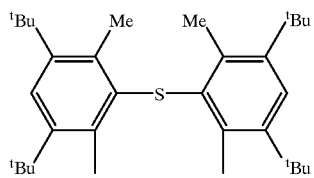
(A-40) 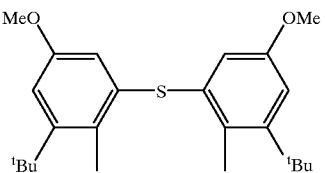
(A-41) 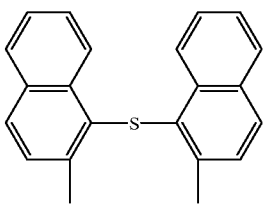

(A-42) 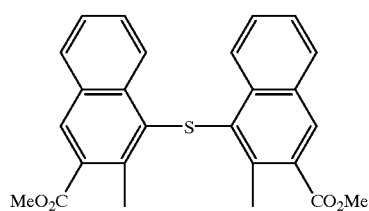
(A-43) 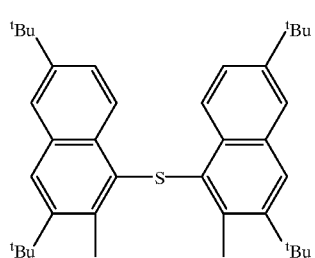
(A-44)
(A-45)
(A-46) 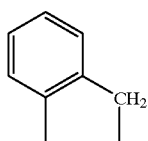
(A 47) 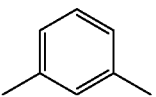
Preferred examples of the compounds (I) through (VI) include the following (1) through (11) and (P1) through (P21).
(1) 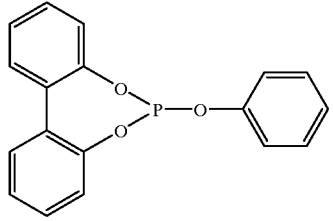
(2) 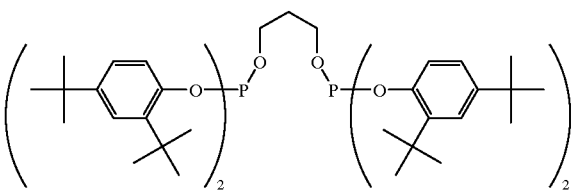
(3) 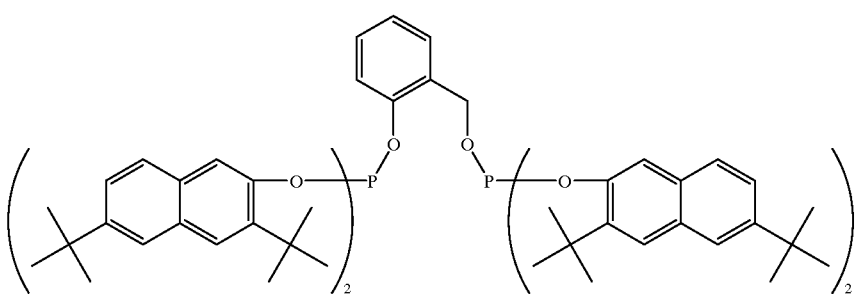

-continued
(4)
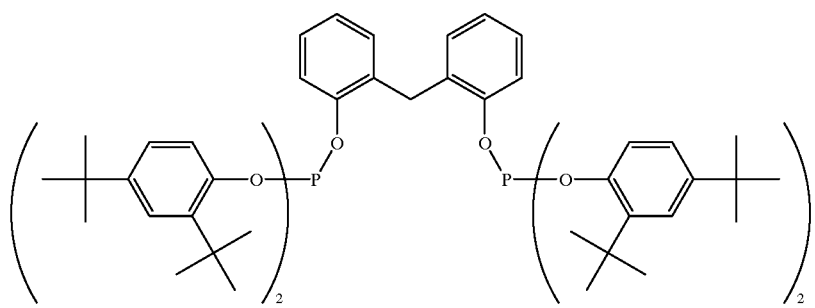
(5)
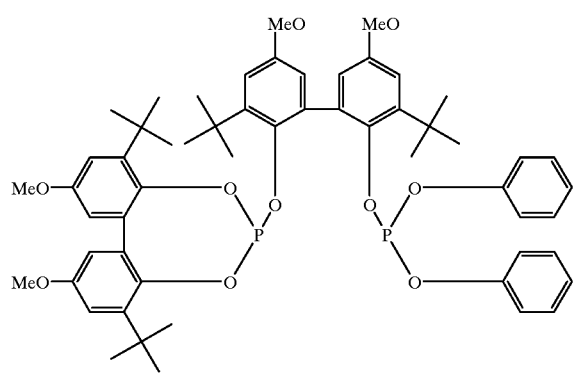
(6)
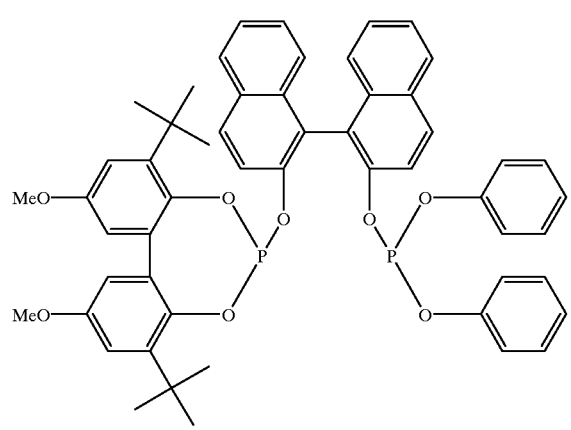
(7)
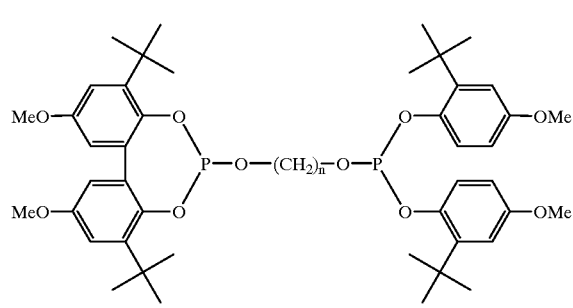
(8)
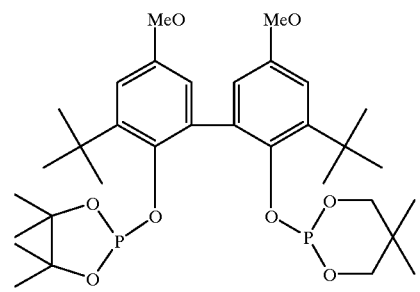
(9)
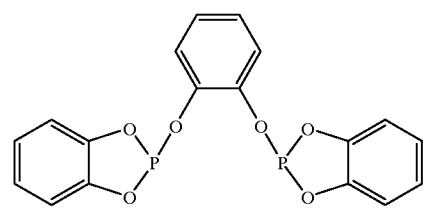
(10)
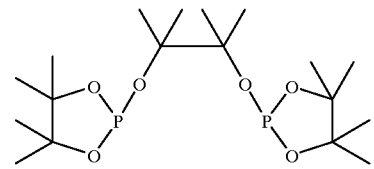

(11)
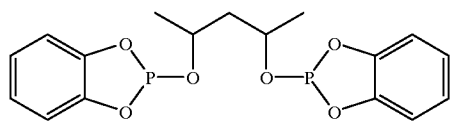
-continued
(P1)
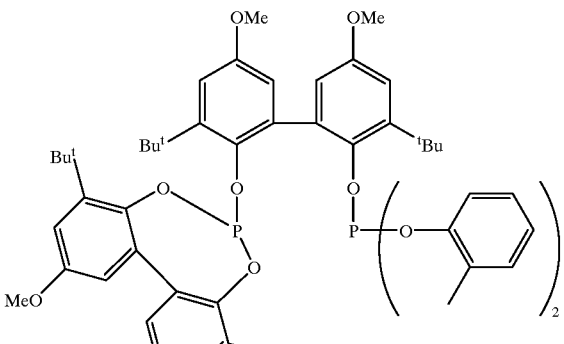
(P2)
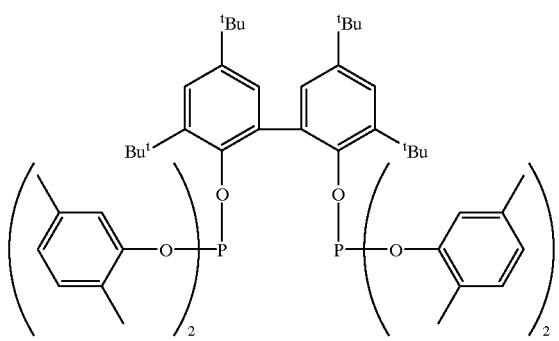
(P3)
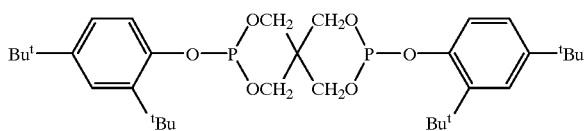
(P4)
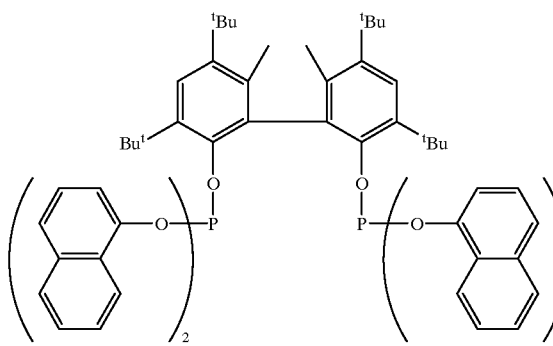
(P5)
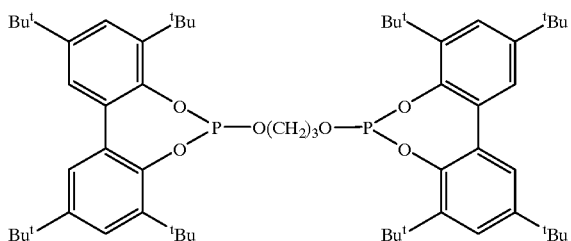
(P6)
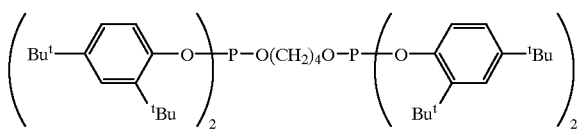
(P7)
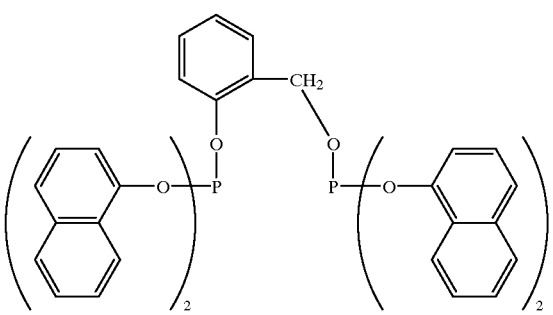

(P8)
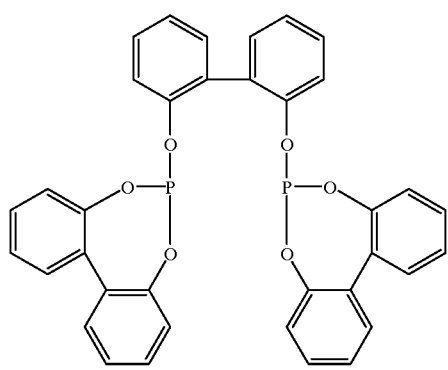
(P9)
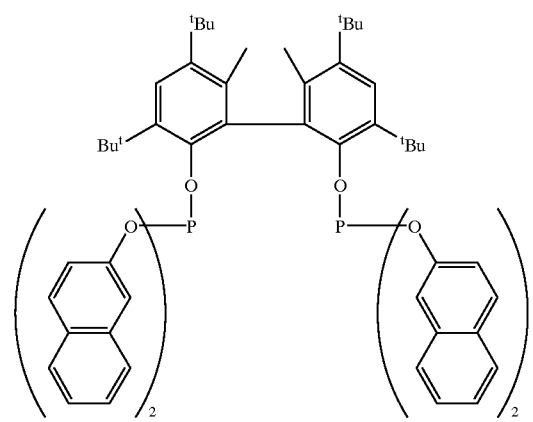
(P10)
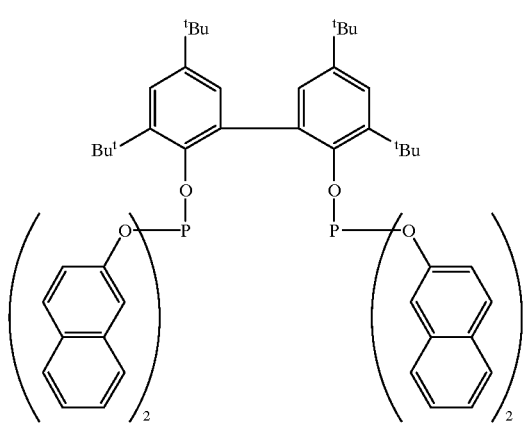
(P11)
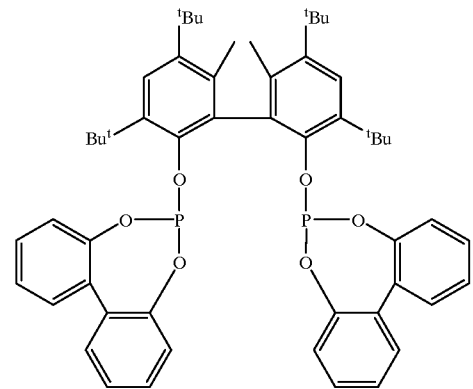
(P12)
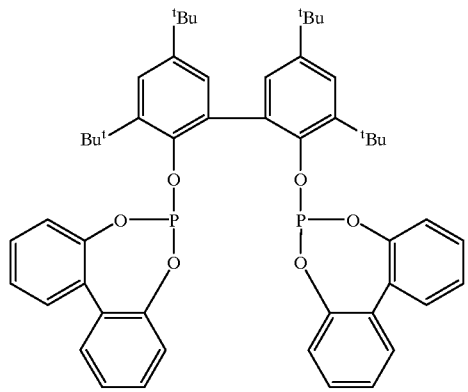
(P13)
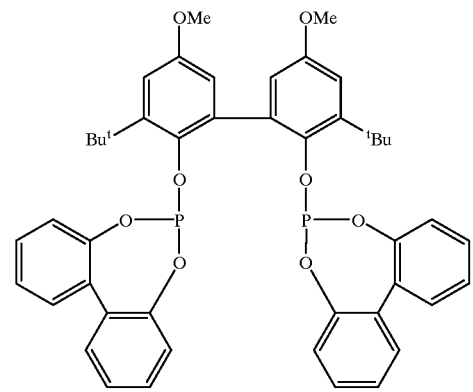

-continued (P14)
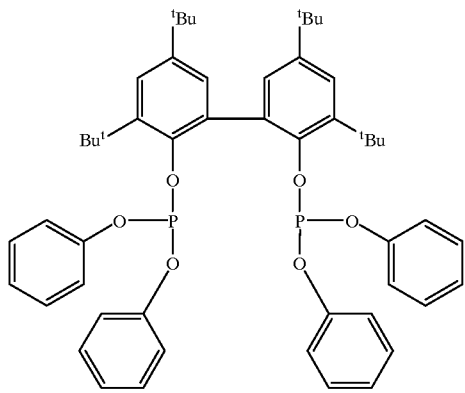

(P15)
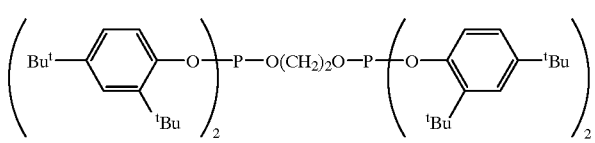

(P16)
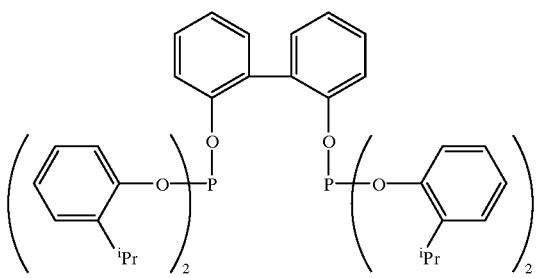

(P17)
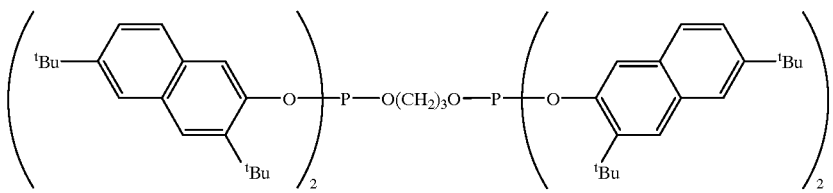

(P18)
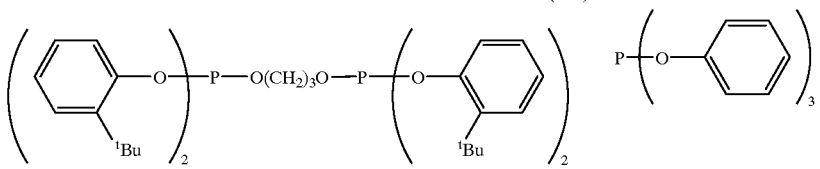

(P19)

(P20)
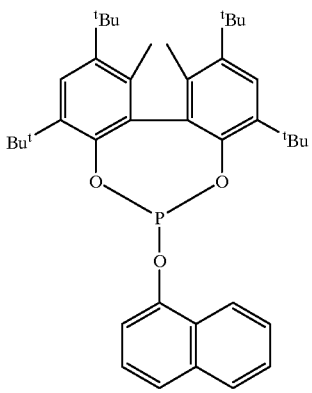

(P21)
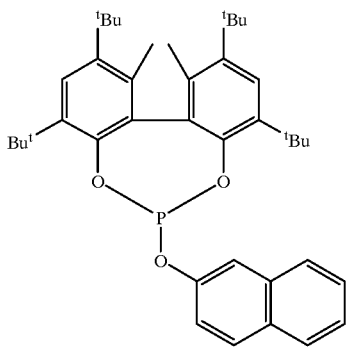

In the isomerization reaction system, the ratio (molar ratio) of the aforementioned phosphite compounds to the above-described metal compound is preferably within a range of 0.1 to 10000, more preferably of 0.5 to 500, and particularly preferably of 1.0 to 100. Each of the above-described metal compounds and phosphite compounds may be added separately, or may be complexed before use.

The isomerization reaction is preferably conducted in the presence of a $C_2$–$C_8$ carboxylic acid, such as aliphatic or aromatic acid, as a co-catalyst or promoter, and more preferably includes aliphatic acid such as acetic acid, propionic acid and butyric acid, and most preferably includes acetic acid. When combined with the specific metal compound and phosphite compound, the isomerization reaction is preferably promoted. The preferable amount of the carboxylic acid is, in terms of the ratio (by weight) of the carboxylic acid to the total amount of allylic substrate, within a preferable range of 10:1 to 1:1000, more preferably 5:1 to 1:500, more preferably 4:1 to 1:100, further preferably of 2:1 to 1:100, from the standpoints of catalyst activity, catalyst stability and economy of the process.

The isomerization reaction can be carried out either in the presence or absence of a solvent, and it is usually preferable that a solvent is used and that the reaction is effected in a uniform system. As the solvent, those dissolving the catalyst and raw material compounds can be used, and they are not particularly limited.

Preferable examples of the solvent include carboxylic acids such as acetic acid and the like, alcohols such as methanol and the like, ethers such as diglyme, diphenyl ether, dibenzyl ether, tetrahydrofuran (THF), dioxane and the like, amides such as N-methylpyrrolidone (NMP), dimethylfomamide (DMF), dimethylacetamide and the like, ketones such as cyclohexanone and the like, esters such as butyl acetate, γ-butyrolactone, di(n-octyl) phthalate and the like, aromatic hydrocarbons such as toluene, xylene, dodecylbenzene and the like, materials having higher boiling points produced as by-products in the isomerization reaction system, raw material allylic compounds themselves and the like. Carboxylic acids such as acetic acid are preferable since it is believed to promote the isomerization reaction. Combinations of solvents are also possible.

The amount of solvent is not particularly restricted, and is preferably from 0.1 to 20-fold by weight, and more preferably 0.5 to 10-fold by weight based on the total amount of allylic substrates.

In the present invention, the reaction for obtaining 1,4-diacetoxy-2-butene by isomerization of 3,4-diacetoxy-1-butene is an equilibrium reaction, with the equilibrium mixture at 120° C. containing approximately 60–65 mol % 1,4-diacetoxy-2-butene together with 35–40 mol % 3,4-diacetoxy-1-butene. This means that a reaction mixture containing mainly 1,4-diacetoxy-2-butene can also be isomerized to produce mainly 3,4-diacetoxy-1-butene. The isomerization reaction is preferably performed to produce a reaction mixture having molar ranges of 1,4-diacetoxy-2-butene to 3,4-diacetoxy-1-butene isomer between 90:10 and 10:90, and may include any ratio therebetween, including 80:20, 70:30, 60:40, 50:50, 40:60, 30:70, and 20:80. This ratio is not particularly restricted and is based on the reaction conditions and the economy of the process.

The isomerization reaction system of the present invention may contain reaction by-products other than raw materials and substrates, decomposed materials of catalysts and the like.

Any of the aforementioned compounds having the formula (a'), (a), (b'), (b), one or more compounds (C) selected from the group including butanediol monoacetoxylate, 1-acetoxybutane-2-one, 4-acetoxybutanal, 4-acetoxycrotonaldehyde, diacetoxybutane, acetoxyhydroxybutane, butanediol, 1,4-butenediol, 1,2-butenediol, 1-acetoxy-1,3-butadiene and diacetoxyoctadiene and mixtures thereof may be present in the isomerization reaction system.

These compounds (C) may exist in the isomerization reaction system in weight ratio to the total amount of allylic substrates (compound (C): allylic compound) within a range preferably of 1:1 to 1:10000, more preferably of 5:1 through 1:1000, more particularly preferably of 2:1 through 1:500, and further preferably of 0.1:through 1:100.

In the present invention, it is preferable that the existing amount of water is small with respect to the reaction mixture, since when a large amount of water exists in the isomerization reaction system, the isomerization reaction may be disturbed. However, complete removal of water from solvent and/or reaction materials requires a large amount of energy. Therefore, the preferable amount of water in the isomerization reaction system (reaction mixture) is, from an industrial point of view, more preferably from 0.1 to 5 wt %, and further preferably from 0.5 to 2 wt %.

Water may enter into the reaction system from various routes. Among them, a carboxylic acid which is used as a solvent or an accelerator of the isomerization reaction often accompanies water. In this case, the ratio of water to carboxylic acid is preferably 1 or less by weight ratio.

The present invention is especially effective when a reaction solution mainly composed of 3,4-diacetoxy-1-butene is separated from a reaction product containing 1,4-diacetoxy-2-butene and 3,4-diacetoxy-1-butene (preferably obtained by diacetoxylation of butadiene in the presence of acetic acid and oxygen, as described above), then the separated reaction solution is isomerized by the process of the present invention to obtain 1,4-diacetoxy-2-butene.

Preferably, the allylic substrate includes a mixture of mainly 3,4-diacetoxy-1-butene and 3-butene-1,2-diol monocarboxylate. In addition, the corresponding allylic isomer preferably includes a mixture of mainly 1,4-diacetoxy-2-butene and 1-acetoxy-4-hydroxy-2-butene. The term mainly, used in this context herein, preferably means at least 50 wt. %, based on the total weight of the reaction mixture, more preferably at least 60 wt. %, more particularly preferably at least 70 wt. %, most preferably at least 80 wt. %, most particularly preferably at least 90 wt. %.

When the reaction product obtained, for example, by a diacetoxylation reaction of butadiene is used as the raw material, the same compounds as the aforementioned compound (C) may be present, in addition to diacetoxy compounds such as 1,4-diacetoxy-2-butene, 3,4-diacetoxy-1-butene and the like. Accordingly, it is preferable to further separate the mixture containing a 3,4-disubstituted-1-butene compound a 1,4-disubstituted-2-butene compound as main component, and then conduct the isomerization reaction of this mixture.

The mixture containing a 3,4-disubstituted-1-butene compound or a 1,4-disubstituted-2-butene compound thus separated by, for example, distillation and the like contains a diacetoxy compound and a monoacetoxy compound. However, the monoacetoxy compound has significantly lower isomerization reaction speed as compared with the diacetoxy compound. Therefore, when such a mixture of a diacetoxy compound and a monoacetoxy compound is isomerized, it is preferable to adopt a method (1) in which the acetoxylation reaction (esterification reaction) of the monoacetoxy compound is conducted before the isomerization reaction, then a mixture containing the resulting diacetoxy compound is isomerized, or a method (2) in which the acetoxylation reaction (esterification reaction) of the monoacetoxy compound is conducted simultaneously in the isomerization reaction system.

The acetoxylation reaction (esterification reaction) of the above-described monoacetoxy compound, for example, 3-butene-1,2-diol monoacetoxylate and/or 1-acetoxy-4-hydroxy-2-butene and the like proceeds in the presence of acetic anhydride. The amount of acetic anhydride is not particularly restricted, and it is preferably around equimolar to the monoacetoxy compound. When acetic anhydride is used, the reaction temperature of the esterification reaction is preferably from 40 to 200° C., more preferably from 100 to 160° C.

Preferably, the above-described acetoxylation reaction (esterification reaction) of a monoacetoxy compound may also proceed in the presence of an ion-exchange resin and acetic acid. Use of an ion-exchange resin is preferable since the acetoxylation reaction can be conducted without using expensive acetic anhydride. The amount of acetic acid is not particularly restricted, however, since the reaction is an equilibrium reaction, the larger the amount of acetic acid, the greater the improvement in the conversion of the acetoxylation reaction.

As the ion-exchange resin which can be adopted, cation-exchange resins such as styrene-based, methacrylic acid-based, acrylic acid-based resins and the like are preferred, and among them, styrene-based cation exchange resin are most preferable. The amount of ion-exchange resin is not particularly restricted, and is preferably 0.01 to 5 kg per kg of allylic substrate, more preferably 0.05 to 1 kg per kg of allylic substrate, for a batch reaction; or preferably the space volume (SV) is 0.05 to 10 liters per liter of allylic substrate per hour, more preferably 0.2 to 2 liters per liter of allylic substrate per hour, for a continuous reaction from the standpoints of catalyst activity and economy. When acetic acid is used, the reaction temperature of the esterification reaction is preferably from 20 to 200° C., more preferably from 30 to 120° C., and most preferaby from 40 to 100° C.

If the method (2) in which the acetoxylation reaction (esterification reaction) of a monoacetoxy compound is conducted simultaneously with the isomerization is adopted, the isomerization reaction and esterification reaction is preferably conducted under the same reaction conditions, preferably, under the above-described isomerization reaction condition in the existence of aforementioned acetic anhydride, or the ion-exchange resin and acetic acid.

The isomerization method of the present invention can be conducted in any of either the batch-wise modes and continuous modes. In addition, any of the steps in the present invention may be conducted continuously or batchwise.

When the isomerization reaction is conducted in a batch-wise mode, a more preferable procedure is as follows: catalyst constituent components are dissolved in a solvent under stirring, the raw material containing 3,4-diacetoxy-1-butene mainly, for example, is introduced into this and allowed to contact the catalyst for an appropriate time for sufficient conversion. After completion of the reaction, the intended product containing mainly 1,4-diacetoxy-2-butene and the like can be separated and recovered from the reaction solution by means of distillation and/or extraction and the like.

In the case of the continuous mode, a preferable method is carried out in which 3,4-diacetoxy-1-butene and catalyst components are continuously fed into a reaction vessel, a reaction solution contains the intended product, the isomerized compound is continuously removed before distillation thereof, and a remaining solution containing the catalyst components is continuously circulated to the reaction system for re-use. The isomerization reaction temperature is preferably from 50 to 200° C., and more preferably from 80 to 160° C. Although the temperature is not particularly limited, when the reaction temperature is too low, the activity may be low, and when too high, the stability of the catalyst may be low and undesirable side-reactions may occur. The isomerization reaction pressure is not particularly restricted, and is preferably selected within a range of normal pressure (atmospheric) through 3 MPa, preferably of normal pressure through 2 MPa. Also, the reaction time is not particularly restricted, and may be appropriately selected in view of the reaction speed depending on factors such as the amount of catalyst, the reaction temperature and the like.

The reaction for isomerization of a 3,4-disubstituted compound to obtain the corresponding 1,4-disubstituted compound is an equilibrium reaction, and the catalyst plays a role in bringing the reaction raw material composition nearer to the equilibrium composition. This effect is identical when the starting material is either a 3,4-disubstituted compound or 1,4-disubstituted compound. Therefore, 1,4-diacetoxy-2-butene can be produced according to the isomerization reaction of 3,4-diacetoxy-1-butene, and, conversely, 3,4-diacetoxy-1-butene can be produced according to the isomerization reaction of 1,4-diacetoxy-2-butene.

According to the present invention, in isomerizing a 3,4-disubstituted-1-butene and/or a 1,4-disubstituted-2-butene in the presence of a catalyst containing a Group VIII to X metal compound, the isomerization product can be obtained in a yield of 10 mol % or more while suppressing the deposition of the metal compound.

The isomerization of the present invention can realize the isomerization of a compound having at the allylic position an acyloxyl group or a hydroxyl group to produce the corresponding respective isomers suppressing the deposition of the metal compound. Accordingly, another preferable embodiment of the invention is industrially advantageously combined with a process of the diacetoxylation of butadiene to produce 1,4-diacetoxy-2-butene.

Preferably, this process includes:

(1) diacetoxylating butadiene to obtain a mixture containing at least one selected from the group including 3,4-diacetoxy-1-butene, 3-butene-1,2-diolmonoacetoxylate and a mixture thereof, and at least one selected from the group including 4-diacetoxy-2-butene, 1-acetoxy-4-hydroxy-2-butene and a mixture thereof;

(2) separating, from the mixture, a portion containing at least one selected from the group including said 3,4-diacetoxy-1-butene, said 3-butene-1,2-diolmonoacetoxylate, and a mixture thereof;

(3) isomerizing at least a part of the portion in the presence of a catalyst, to obtain an isomerization product mixture;

(4) optionally, recirculating at least a part of the isomerization product mixture to at least one selected from the group including the isomerizing, the separating, the mixture, and combinations thereof.

Another preferable embodiment of the present invention is also industrially advantageously combined with a process of the diacetoxylation of butadiene to produce 1,4-diacetoxy-2-butene.

Preferably, this process includes:

(1) diacetoxylating butadiene {Acetoxylation step}

(2) separating a portion of mainly containing 3,4-diacetoxy-1-butene and/or 3-butene-1,2-diolmonoacetoxylate from a residue containing 1,4- diacetoxy-2-butene and/or acetoxy-4-hydroxy-2-butene {Separation step}

(3) conducting the isomerization reaction of at least a part of the portion of mainly containing 3,4-diacetoxy-1-butene and/or 3-butene-1,2-diolmonoacetoxylate from the Separation step in the presence of a catalyst, {Isomerization reaction step}

(4) optionally, before the Isomerization reaction step or during the isomerization reaction step, conducting the esterification reaction of the part of the portion of mainly containing 3,4-diacetoxy-1butene and/or 3-butene-1,2-diolmonoacetoxylate {Esterification step}

(5) circulating at least a part of the isomerization reaction products to the isomerization step or any of the previous steps {Circulation step}.

In the above preferred embodiments, the catalyst is not particularly limited, and may include any known catalyst for isomerizing an allylic substrate having at the allyl position an acyloxyl or a hydroxyl group. Preferable catalysts for this embodiment of the invention include those discussed in the Background section of this application, incorporated herein by reference. Most preferably, however, the catalyst includes the aforementioned catalyst containing a Group VIII through X metal compound and a phosphite compound.

The isomerization reaction system in the above preferred embodiments may contain reaction by-products other than raw materials and substrates, decomposed materials of catalysts and the like. These preferably include any of the aforementioned formula (a'), formula (a), formula (b'), formula (b), one or more compounds (C) selected from butanediol monoacetoxylate, 1-acetoxybutane-2-one, 4-acetoxybutanal, 4-acetoxycrotonaldehyde, diacetoxybutane, acetoxyhydroxybutane, butanediol, 1-acetoxy-1,3-butadiene and diacetoxyoctadiene and mixtures thereof may be present in the isomerization reaction system.

The isomerization reaction products can be removed from the reaction vessel, and a residue containing catalyst components can be separated by conventional methods, for example, distillation or extraction from the isomerization reaction products and recycled to the Isomerization step and/or Separation step and/or any of the other steps. The catalyst components of the isomerization reaction can also be recovered from the residue of the distillation and re-generated and/or re-used as appropriate.

Other preferable embodiments include an equilibrium mixture produced according to the process of the present invention and corresponding allylic isomer(s) produced according to the process of the present invention.

EXAMPLES

Having generally described this invention, a further understanding can be obtained by reference to certain specific examples which are provided herein for purposes of illustration only and are not intended to be limiting unless otherwise specified. The reaction results in the following examples were calculated based on the results obtained by analyzing the composition of a reaction solution by gas chromatography. All reactions which included the use of phosphites were performed under a nitrogen atmosphere.

When 3,4-diacetoxy-1-butene (hereinafter, sometimes abbreviated as 3,4-DABE) is used as the raw material, no other compound than 1,4-diacetoxy-2-butene (hereinafter, sometimes abbreviated as 1,4-DABE) can be detected as the product, therefore, the yield of 1,4-diacetoxy-2-butene is regarded as the reaction result. As phosphite compounds, (P1) through (P21) as described above were used.

Examples 1 Through 8

Into 10 ml flask purged with nitrogen were added 3,4-diacetoxy-1-butene (0.633 mmol), $Pd(OAc)_2$ (0.0221 mmol), the above-described phosphite compound (0.041 mmol) and acetic acid (1 ml), and reacted for 1 hour at 80° C. The yield of 1,4-diacetoxy-2-butene (1,4-DABE) is shown in Table 1. In any system, no deposition of Pd metal was observed.

TABLE 1

| | Phosphite compound | 1,4-DABE yield (%) |
|---|---|---|
| Example 1 | (P1) | 67 |
| Example 2 | (P2) | 65.1 |
| Example 3 | (P3) | 64.2 |
| Example 4 | (P4) | 62 |
| Example 5 | (P5) | 59.8 |
| Example 6 | (P6) | 46.5 |
| Example 7 | (P7) | 10.6 |
| Example 8 | (P8) | 47.2 |

Example 9

The same reaction as Example 3 was conducted except that 1 ml of diglyme was used instead of acetic acid used in Example 3 and the reaction temperature was changed to 120° C., to find a yield of 1,4-DABE of 56.5%. Also in this case, no deposition of palladium metal was observed.

Example 10

The same reaction as Example 9 was conducted except that $P(OPh)_3$ (0.082 mmol) was used instead of (P3) used in example 9 and the reaction temperature was changed from 120° C. to 100° C., to find a yield of 1,4-DABE of 10.9%. No deposition of palladium metal was observed.

Example 11

$Pd(OAc)_2$ (0.633 mmol), (P3) as a phosphite compound (0.041 mmol), acetic acid (0.037 ml), 1 ml of diglyme and 0.633 mmol of 3,4-diacetoxy-1-butene (3,4-DABE) or 1,4-diacetoxy-2-butene (1,4-DABE) were charged, and reacted at 68° C. The results are shown in FIG. 1. In any raw material, it was proved that the isomerization reaction was completed in about 100 minutes to reach the equilibrium concentration. In this case, no deposition of palladium was observed providing a phosphite compound was present.

Examples 12 to 14

(Pd System, P19 to 21 were Used)

Into 1 ml (6.3 mmol) of 3,4-diacetoxybutene-1 were dissolved 21 μmol (5 mg) of $Pd(OAc)_2$ and the above-described phosphite compounds (P19) through (P21) in each amount of 12 mg, then, acetic acid (10 μl) was added and reacted for 30 minutes at 120° C. The results are shown in the following Table 2. In any system, no deposition of Pd metal was observed.

TABLE 2

| Ligand | Molar balance (%) | 1,4-DABE (%) | Trans/Cis |
|---|---|---|---|
| P19 | 95 | 11 | 11.2 |
| P20 | 95 | 38 | 7.7 |
| P21 | 81 | 55 | 6.0 |

Example 15

(Pd System, P13 was Used)

3.7 mg (6.4 μmol) of Pd(dba)$_2$ and 40 mg (51 mmol) of the above-described phosphite compound (P13) were added to 1 ml (6.3 mmol) of 3,4-diacetoxybutene-1. Then 10 μl of this solution was added to a separate Schlenk tube containing acetic acid (1 ml) and 1 ml (6.3 mmol) of 3,4-diacetoxybutene-1, and reacted for 3 hours at 120° C. The molar balance is 99% or more, and the reaction product solution was analyzed to find 62% of 1,4-DABE and 38% of 3,4-DABE contained. Also, in this reaction, no deposition of Pd metal was observed.

Example 16

(Influence by Amount of Acetic Acid)

Pd(OAc)$_2$ having molar concentrations relative to 3,4-DABE shown in the following Table 3 and 4 mol equivalent of biphosphite (P4) were added to a flask containing acetic acid in amounts shown in Table 3 and 1 ml (6.3 mmol) of 3,4-DABE, and reacted for 1 hour at 120° C. The results are shown in Table 3. Also, in this reaction, no deposition of Pd metal was observed.

TABLE 3

| Pd(OAc)$_2$ (ppm) | Acetic acid (ml) | Conversion (%) | Molar balance (%) |
|---|---|---|---|
| 1500* | 0.01 | 52 | 72 |
| 35 | 0.1 | 59 | 98 |
| 17 | 0.1 | 49 | 100 |
| 7 | 0.1 | 29 | 98 |
| 2 | 1.0 | 29 | 99 |

At *, the reaction time was 15 minutes.

At *, the reaction time was 15 minutes.

From the results shown in Table 3, it is known that in the range wherein the concentration of acetic acid is high, namely, wherein the concentration of the Pd compound is low, the molar balance is as high as 98% or more.

Examples 17 Through 28

(Influence by Temperature and Time)

Into 1 ml (6.3 mmol) of 3,4-diacetoxy-1-butene were dissolved 1.5 mg (6.7 μmol) of Pd(OAc)$_2$ and 26.8 μmol of phosphite compounds shown in the following Table 4 at 120° C. Then, 3 μl of this solution was added to a separate flask containing acetic acid (1 ml) and 1 ml (6.3 mmol) of 3,4-diacetoxybutene-1, and reacted either for 1 hour at 120° C. or for 3 hours at 140° C. The results are shown in the following Table 4. The molar balance was 98% or more, and the reaction product solution contained mainly 1,4-DABE and unreacted 3,4-DABE. In any of the systems, no deposition of Pd metal was observed.

TABLE 4

| Example | Ligand | 1,4-DABE (%; 120° C. 1 h) | 1,4-DABE (%; 140° C. 3 h) |
|---|---|---|---|
| Example 17 | P15 | 1 | Not measured |
| Example 18 | P16 | 1 | Not measured |
| Example 19 | P17 | 2 | Not measured |
| Example 20 | P18 | 2 | Not measured |
| Example 21 | P11 | 7 | Not measured |
| Example 22 | P5 | 8 | Not measured |
| Example 23 | P4 | 19 | 35 |
| Example 24 | P1 | 23 | Not measured |
| Example 25 | P10 | 26 | 46 |
| Example 26 | P12 | 25 | 46 |
| Example 27 | P13 | 25 | 44 |
| Example 28 | P9 | 31 | 55 |

At the equilibrium point at 120° C., the reaction mixture contained 63% of 1,4-DABE and 37% of 3,4-DABE.

Example 29

(Pt System, Phosphite P13 was Used)

Into 1 ml (6.3 mmol) of 3,4-diacetoxybutene-1 were dissolved 2.5 mg (6.21 μmol) of Pt(acac)$_2$ and 10 mg (13 μmol) of the above-described phosphite compound (P13), then acetic acid (1 ml) was added and reacted for 1 hour at 120° C. The reaction product solution was analyzed by GC to find 17 mol % of 1,4-DABE (trans/cis=4.5) and 83 mol % of 3,4-DABE. In this reaction, no deposition of Pt metal was observed.

Example 30

(Rh System, Phosphite P13 was Used)

Into 1 ml (6.3 mmol) of 3,4-diacetoxybutene-1 were dissolved 1.8 mg (3.5 μmol) of {Rh(COD)OAc}$_2$ and 10 mg (13 μmol) of the above-described phosphite compound (P13), then acetic acid (1 ml) was added and the solution was reacted for 1 hour at 120° C. The reaction product solution was analyzed by GC to find 6.3 % of 1,4-DABE (trans/cis=4.3) and 92 mol % of 3,4-DABE. In this reaction, no deposition of Rh metal was observed.

Example 31

(Ni System, Phosphite P4 was Used)

Into 1 ml (6.3 mmol) of 3,4-diacetoxybutene-1 were dissolved 8 mg (29 μmol) of Ni(COD)$_2$ and 62 mg (58 μmol) of the above-described phosphite compound (P4). Then, 10 μl of this solution was added to a separate Schlenk tube containing acetic acid (1 ml) and 1 ml (6.3 mmol) of 3,4-diacetoxybutene-1, and reacted for 1 hour at 120° C. The reaction product solution was analyzed to find 0.8% of 1,4-DABE (trans/cis=8.8) and 99% of 3,4-DABE. In this reaction, no deposition of Ni metal was observed.

Example 32

(Isomerization and Esterification)

Into 1 ml of solution containing 75 mol % of 3,4-diacetoxybutene-1 and 25 mol % of 1-butenediol acetoxylate were dissolved 3.7 mg (6.4 μmol) of Pd(dba)$_2$ and 40 mg (51 μmol) of the above-described phosphite compound (P13) at 120° C. Then, 3 μl of this solution was added to a separate solution comprising 1 ml (6.8 mmol) of acetic acid and 1 ml of a solution containing 75 mol % of 3,4-diacetoxy-1-butene and 25 mol % of 1-butenediol monoacetoxylate, and reacted for 3 hours at 120° C. As a result, the isomerization reaction and the esterification reaction progressed, and in the reaction product solution, 82% diacetoxy butenes and 18% of butenediol monoacetoxylates were produced in a selection shown in the following Table 5.

TABLE 5

|  | 1,4 selectivity |
|---|---|
| Diacetoxy butenes | 29% |
| Butenediol monoacetoxylates | 14% |

Example 33
Water 0 Weight % Relative to Acetic Acid (Water 0 Weight % Based on the Reaction Mixture)

3.7 mg (6.4 µmol) Pd(dba)$_2$ and 28 mg (26.1 µmol) of P9 was dissolved at 120° C. in 1 ml (6.3 mmol) 3,4-diacetoxy-1-butene. 5 µL of this solution was added to a 1 mL (6.3 mmol) solution of 3,4-diacetoxy-1-butene and the reaction mixture was stirred at 120° C. for 1 hour. Analysis of the reaction mixture showed 41 mol % 1,4-diacetoxy-2-butene and 59 mol % 3,4-diacetoxy-1-butene.

Example 34
Water 1 Weight % Relative to Acetic Acid (Water 0.5 Weight % Based on the Reaction Mixture)

3.7 mg (6.4 µmol) Pd(dba)$_2$ and 28 mg (26.1 µmol) of P9 was dissolved at 120° C. in 1 ml 3,4-diacetoxy-1-butene. 5 µL of this solution was added to a 1 mL solution of 3,4-diacetoxy-1-butene and 10 µL (0.6 µmol) water and the reaction mixture was stirred at 120° C. for 1 hour. Analysis of the reaction mixture showed 34 mol % 1,4-diacetoxy-2-butene and 66 mol % 3,4-diacetoxy-1-butene.

Example 35
Water 2 Weight % Relative to Acetic Acid (Water 1 Weight % Based on the Reaction Mixture)

3.7 mg (6.4 µmol) Pd(dba)$_2$ and 28 mg (26.1 µmol) of P9 was dissolved at 120° C. in 1 ml 3,4-diacetoxy-1-butene. 5 µL of this solution was added to a 1 mL solution of 3,4-diacetoxy-1-butene and 20 µL (1.1 µmol) water and the reaction mixture was stirred at 120° C. for 1 hour. Analysis of the reaction mixture showed 30 mol % 1,4-diacetoxy-2-butene and 70 mol % 3,4-diacetoxy-1-butene.

Example 36
0 Mol % 1-butenediol Monoacetoxylate, 100 Mol % 3,4-diacetoxy-1-butene 3.7 mg (6.4 µmol) Pd(dba)$_2$ and 28 mg (26.1 µmol) of P9 was dissolved at 120° C. in 1 ml (6.3 mmol) 3,4-diacetoxy-1-butene. 5 µL of this solution was added to a 1 mL (6.3 mmol) solution of 3,4-diacetoxy-1-butene and the reaction mixture was stirred at 120° C. for 1 hour. Analysis of the reaction mixture showed 41 mol % 1,4-diacetoxy-2-butene and 59 mol % 3,4-diacetoxy-1-butene.

Example 37
11 Mol % 1-butenediol Monoacetoxylate 89 Mol % 3,4-diacetoxy-1-butene 3.7 mg (6.4 µmol) Pd(dba)$_2$ and 28 mg (26.1 µmol) of P9 was dissolved at 120° C. in 1 ml (6.3 mmol) 3,4-diacetoxy-1-butene. 5 µL of this solution was added to a 1 mL (6.5 mmol) solution of 11 mol % 1-butenediol monoacetoxylate and 89 mol % 3,4-diacetoxy-1-butene and the reaction mixture was stirred at 120° C. for 1 hour. Analysis of the reaction mixture showed 28 mol % 1,4-isomers (1,4-diacetoxy-2-butene and 1-acetoxy-4-hydroxy-2-butene) and 72 mol % 3,4-isomers (3,4-diacetoxy-1-butene and 1-butenediol monoacetoxylate).

Example 38
22 Mol % 1-butenediol Monoacetoxylate, 78 Mol % 3,4-diacetoxy-1-butene 3.7 mg (6.4 µmol) Pd(dba)$_2$ and 28 mg (26.1 µmol) of P9 was dissolved at 120° C. in 1 ml (6.3 mmol) 3,4-diacetoxy-1-butene. 5 µL of this solution was added to a 1 mL (6.7 mmol) solution of 22 mol % 1-butenediol monoacetoxylate and 78 mol % 3,4-diacetoxy-1-butene and the reaction mixture was stirred at 120° C. for 1 hour. Analysis of the reaction mixture showed 21 mol % 1,4-isomers (1,4-diacetoxy-2-butene and 1-acetoxy-4-hydroxy-2-butene) and 79 mol % 3,4-isomers (3,4-diacetoxy-1-butene and 1-butenediol monoacetoxylate).

Reference Example 1
(Esterification of Monoacetoxylates with Acetic Acid)

A solution comprising 1 ml (6.8 mmol) of acetic acid and 1 ml of a solution containing 75 mol % of 3,4-diacetoxy-1-butene and 25 mol % of 3-butene-1,2-diolmonoacetoxylate was reacted for 1 hour at 120° C. As a result, the reaction product solution contained 79% of diacetoxy butenes and 21% of butenediol monoacetoxylates, and no isomerized product was detected.

Such an esterification reaction can be conducted simultaneously with the isomerization reaction, and alternatively, diacetoxy butenes obtained by the esterification reaction may be further isomerized.

Reference Example 2
(Esterification of Monoacetoxylates with Acetic Acid and Ion Exchange Resin)

7.9 g of SK1BH ion exchange resin (manufactured by Mitsubishi Chemical Corporation) was washed with acetic acid, 10 ml (73 mmol) of acetic acid, and 10 ml of a mixed solution containing 44 mol % of 4-acetoxy-3-hydroxy-1-butene, 40 mol % of 3-acetoxy-4-hydroxy-1-butene, 16 mol % of 3,4-diacetoxy-1-butene and 1 mol of 1,4-diacetoxy-2-butene were reacted for 9 hours at 65° C. As a result, the reaction product contained 26 mol % of 4-acetoxy-3-hydroxy-1-butene, 14 mol % of 3-acetoxy-4-hydroxy-1-butene, 52 mol % of 3,4-diacetoxy-1-butene and 8 mol % of 1,4-diacetoxy-2-butene. The amounts produced of diacetoxy butenes (total amount of 3,4-diacetoxy-1-butene and 1,4-diacetoxy-2-butene) at given reaction times are shown in the following Table 6.

TABLE 6

| Time/hour | Diacetoxy butenes (mol %) |
|---|---|
| 0 | 17.1 |
| 1 | 34.5 |
| 2 | 43.5 |
| 3 | 49.1 |
| 4 | 53.5 |
| 5 | 54.8 |
| 6 | 57.3 |
| 7 | 58.9 |
| 9 | 59.8 |

Such an esterification reaction can be conducted simultaneously with the isomerization reaction, and alternatively, diacetoxy butenes obtained by the esterification reaction may be further isomerized.

Reference Example 3
(Esterification of Butenediol Monoacetoxylate with Acetic Anhydride)

To 1 ml of a solution containing 75 mol % of 3,4-DABE and 25 mol % of 3,4-HABE was added 180 µl(0,3 mol equivalent) of acetic anhydride, and reacted for 5 hours at 120° C. As a result, the reaction product solution contained 98 mol % of 3,4-DABE and 2 mol % of 3,4-HABE. The amounts produced of 3,4-DABE and 3,4-HABE at given reaction times are shown in the following Table 7.

TABLE 7

| Time/hour | 3,4-DABE (mol %) | 3,4-DABE (mol %) |
|---|---|---|
| 0 | 75 | 25 |
| 1 | 92 | 7.6 |
| 2 | 95 | 5.0 |
| 3 | 96 | 3.5 |
| 6 | 98 | 2.0 |

Such an esterification reaction can be conducted simultaneously with the isomerization reaction, and alternatively, diacetoxy butenes obtained by the esterification reaction may be further isomerized.

Comparative Example 1

In 10 ml of a flask purged with nitrogen, 3,4-diacetoxy-1-butene (0.633 mmol), Pd(OAc)$_2$ (0.066 mmol) and 1 ml of diglyme were used, and reacted for 1 hour at a reaction temperature of 120° C., to find a yield of 1,4-DABE of 1.3%. However, a metal mirror of Pd was observed on the surface of the flask after completion of the reaction.

Comparative Example 2

The same reaction was conducted as in Comparative Example 1 except that PdCl$_2$ (0.06 mmol) was used instead of Pd(OAc)$_2$ used in Comparative Example 1. As a result, the yield of 1,4-DABE was 58%. However, a metal mirror of palladium was observed on the surface of the flask after completion of the reaction.

Comparative Example 3

The same reaction was conducted as in Comparative Example 1 except that PdCl2(PPh$_3$)$_2$ (0.06 mmol) was used instead of Pd(OAc)$_2$ used in Comparative Example 1. However, no production of 1,4-DABE was detected.

According to the present invention, if allylic compounds such as 3,4-disubstituted-1-butene and/or 1,4-disubstituted-2-butene and the like are isomerized using a catalyst containing a Group VIII through X metal compound and a phosphite compound, the corresponding isomers 1,4-disubstituted-2-butene and/or 3,4-disubstituted-1-butene can be produced at high conversion and high selectivity without causing deposition of metals.

Obviously, numerous modifications and variations of the present invention are possible in light of the above teachings. It is therefore to be understood that within the scope of the appended claims, the invention may be practiced otherwise than as specifically described herein.

All patents and other references mentioned above are incorporated in full herein by this reference, the same as if set forth at length.

This application is based on Japanese Application No. JP 11-107568, filed Apr. 15, 1999, the entire contents of which are hereby incorporated by reference.

What is claimed is:

1. A process, comprising:
 isomerizing at least one allylic substrate having an acyloxyl group or a hydroxyl group at the allyl position thereof, to produce a corresponding allylic isomer, wherein said isomerizing is conducted in the presence of a catalyst comprising a Group VIII-X metal compound and a phosphite compound.

2. The process according to claim 1, wherein said acyloxyl group is an acetoxyl group —O(O)CCH$_3$.

3. The process according to claim 1, wherein said allylic substrate is at least one selected from the group consisting of the following formula (a), (b), and a mixture thereof:

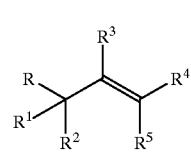

Formula (a)

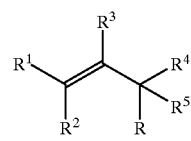

Formula (b)

wherein R represents an acyloxyl group or a hydroxyl group; each substituent $R^1$ through $R^5$, independently of one another, represents at least one selected from the group consisting of a hydrogen atom, a hydroxyl group, a halogen atom, a cyano group, optionally substituted $C_1$–$C_{20}$ alkyl, optionally substituted $C_1$–$C_{20}$ alkoxy, optionally substituted $C_3$–$C_{20}$ cycloalkyl, optionally substituted di-$C_1$–$C_{20}$ alkylamino, optionally substituted $C_6$–$C_{20}$ aryl, optionally substituted $C_6$–$C_{20}$ aryloxy, optionally substituted $C_6$–$C_{20}$ alkylaryl, optionally substituted $C_6$–$C_{20}$ alkylaryloxy, optionally substituted $C_6$–$C_{20}$ arylalkoxy group, optionally substituted $C_2$–$C_{20}$ ester and combinations thereof.

4. The process according to claim 1, wherein said corresponding allylic isomer is at least one selected from the group consisting of the following formula (b), (a), and a mixture thereof:

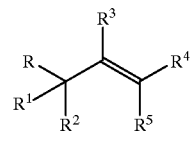

Formula (a)

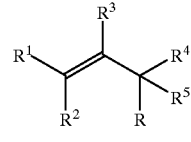

Formula (b)

wherein R represents an acyloxyl group or a hydroxyl group; each substituent $R^1$ through $R^5$, independently of one another, represents at least one selected from the group consisting of a hydrogen atom, a hydroxyl group, a halogen atom, a cyano group, optionally substituted $C_1$–$C_{20}$ alkyl, optionally substituted $C_1$–$C_{20}$ alkoxy, optionally substituted $C_3$–$C_{20}$ cycloalkyl, optionally substituted di-$C_1$–$C_{20}$ alkylamino, optionally substituted $C_6$–$C_{20}$ aryl, optionally substituted $C_6$–$C_{20}$ aryloxy, optionally substituted $C_6$–$C_{20}$ alkylaryl, optionally substituted $C_6$–$C_{20}$ alkylaryloxy, optionally substituted $C_6$–$C_{20}$ arylalkoxy group, optionally substituted $C_2$–$C_{20}$ ester and combinations thereof.

5. The process according to claim 1, wherein said allylic substrate is selected from the group consisting of a 3,4-disubstituted-1-butene of the formula (a'): $CH_2=CH-CHR^6-CH_2R^7$, a 1,4-disubstituted-2-butene of the formula (b'): $CH_2R^8-CH=CH-CH_2R^9$, and a mixture thereof, wherein each of $R^6$ to $R^9$ is independently a group selected from the group consisting of an acyloxyl group and a hydroxyl group.

6. The process according to claim 5, wherein said (a') is isomerized to produce a 1,4-disubstituted-2-butene of the formula (b'): $CH_2R^8-CH=CH-CH_2R^9$, wherein each of $R^6$ to $R^9$ is independently a group selected from the group consisting of an acyloxyl group and a hydroxyl group.

7. The process according to claim 5, wherein said (b') is isomerized to produce a 3,4-disubstituted-1-butene of the formula (a'): $CH_2=CH-CHR^6-CH_2R^7$, wherein each of $R^6$ to $R^9$ is independently a group selected from the group consisting of an acyloxyl group and a hydroxyl group.

8. The process according to claim 1, wherein said allylic substrate is selected from the group consisting of 3,4-diacetoxy-1-butene, 1,4-diacetoxy-2-butene, and a mixture thereof; and wherein said corresponding allylic isomer is selected from the group consisting of, respectively, 1,4-diacetoxy-2-butene, 3,4-diacetoxy-1-butene, and a mixture thereof.

9. The process according to claim 1, wherein said allylic substrate is selected from the group consisting of 3-butene-1,2-diol monoacetoxylate, 1-acetoxy-4-hydroxy-2-butene, and a mixture thereof; and wherein said corresponding allylic isomer is selected from the group consisting of, respectively, 1-acetoxy-4-hydroxy-2-butene, 3-butene-1,2-diol monocarboxylate, and a mixture thereof.

10. The process according to claim 9, wherein said 3-butene-1,2-diol monoacetoxylate is at least one selected from the group consisting of 4-acetoxy-3-hydroxy-1-butene, 3-acetoxy-4-hydroxy-1-butene, and a mixture thereof.

11. The process according to claim 1, wherein said allylic substrate comprises a mixture of 3,4-diacetoxy-1-butene and 3-butene-1,2-diol monocarboxylate; and wherein said corresponding allylic isomer comprises a mixture of 1,4-diacetoxy-2-butene and 1-acetoxy-4-hydroxy-2-butene.

12. The process according to claim 1, wherein said metal compound is at least one selected from the group consisting of rhodium compounds, ruthenium compounds, nickel compounds, platinum compounds, palladium compounds, and mixtures thereof.

13. The process according to claim 1, wherein said metal compound is a palladium compound.

14. The process according to claim 1, wherein said phosphite compound is at least one selected from the group consisting of compounds of the following formulae (I), (II), (III), (IV), (V), (VI), and mixtures thereof:

$P(OR^{10})(OR^{11})(OR^{12})$ (I)

 (II)

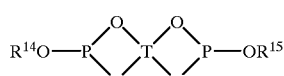 (III)

 (IV)

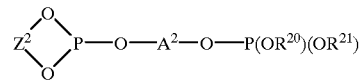 (V)

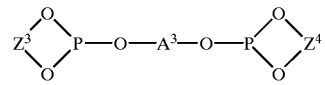 (VI)

wherein each $R^{10}$ through $R^{21}$, independently of one another, represents an alkyl, alkoxy, cycloalkyl, aryloxy, alkylaryloxy, arylalkoxy, or aryl group, each group optionally having one or more substituents;

each $Z^1-Z^4$, independently of one another, represents a $C_1-C_{20}$ alkylene group optionally having one or more substituents, a $C_6-C_{30}$ arylene group optionally having one or more substituents or a $C_{12}-C_{40}$ diarylene group, $-Ar^1-(Q^1)_n-Ar^2-$, wherein each $Ar^1$ and $Ar^2$, independently of one another, represents a $C_6-C_{18}$ arylene group optionally having one or more substituents;

each $A^1-A^3$, independently of one another, represents a $C_1-C_{20}$ alkylene group optionally having one or more substituents, a $C_6-C_{30}$ arylene group optionally having one or more substituents or a $C_{12}-C_{40}$ diarylene group, $-Ar^1-(Q^1)_n-Ar^2-$, wherein each $Ar^1$ and $Ar^2$, independently of one another, represents a $C_6-C_{18}$ arylene group optionally having one or more substituents;

T represents a carbon atom, alkanetetrayl group, benzenetetrayl group or a tetravalent group of $T^1-(Q^2)_n-T^2$ optionally having one or more substituents, wherein each $T^1$ and $T^2$, independently of one another, represents the same or different trivalent organic group, which may each independently have one or more substituents;

each $Q^1$ and $Q^2$, independently of one another, represents $-CR^{22}R^{23}-$, $-O-$, $-S-$ or $-CO-$, wherein each $R^{22}$ and $R^{23}$, independently of one another, represents a hydrogen atom, $C_1-C_{10}$ alkyl or $C_6-C_{10}$ aryl group, each optionally having one or more substituents, and n is 0 or 1.

15. The process according to claim 14, wherein said phosphite compound is a compound of the formula (IV).

16. The process according to claim 14, wherein said phosphite compound is a compound of the formula (V).

17. The process according to claim 14, wherein said phosphite compound is a compound of the formula (VI).

18. The process according to claim 14, wherein in any of the formulae (IV) to (V), each $R^{16}$ through $R^{21}$, independently of one another, represents a $C_6-C_{20}$ aryl group optionally having one or more substituents; each $Z^1-Z^4$, independently of one another, represents a $C_{12}-C_{40}$ diarylene group, $-Ar^1-(Q^1)_n-Ar^2-$, wherein each $Ar^1$ and $Ar^2$, independently of one another, represents a $C_6-C_{18}$ arylene group optionally having one or more substituents; each $Q^1$, independently of one another, represents $-CR^{22}R^{23}-$, $-O-$, $-S-$ or $-CO-$, wherein each $R^{22}$ and $R^{23}$, independently of one another, represents a hydrogen atom, $C_1-C_{10}$ alkyl or $C_6-C_{10}$ aryl group, each optionally having one or more substituents, and n is 0 or 1.

19. The process according to claim 1, wherein a molar ratio of said metal compound to said phosphite compound ranges from 1:0.1 to 1:10000.

20. The process according to claim 1, wherein said isomerizing is conducted in a liquid phase.

21. The process according to claim 1, wherein said isomerizing is conducted in at least one solvent selected from the group consisting of carboxylic acids, alcohols, ethers, amides, ketones, esters, aromatic hydrocarbons, materials having higher boiling points produced as by-products in said isomerizing, raw material allylic compounds, and mixtures thereof.

22. The process according to claim 1, wherein said isomerizing is conducted in at least one solvent selected from the group consisting of acetic acid, methanol, diglyme, diphenyl ether, dibenzyl ether, tetrahydrofuran (THF), dioxane, N-methylpyrrolidone (NMP), dimethylformamide (DMF), dimethylacetamide, ketones, cyclohexanone, butyl acetate, γ-butyrolactone, di(n-octyl) phthalate, toluene, xylene, dodecylbenzene, and mixtures thereof.

23. The process according to claim 1, wherein said isomerizing is carried out at a reaction temperature of 50–200° C.

24. The process according to claim 1, wherein said isomerizing is carried out at a reaction pressure ranging from atmospheric pressure to 3 MPa.

25. The process according to claim 1, further comprising carrying out said isomerizing in the presence of at least one $C_2$–$C_8$ carboxylic acid.

26. The process according to claim 25, wherein said $C_2$–$C_8$ carboxylic acid is acetic acid.

27. The process according to claim 25, wherein said $C_2$–$C_8$ carboxylic acid is present in said isomerizing in a weight ratio ranging from 10:1 to 1: 1000, based on the total weight of said allylic substrate.

28. The process according to claim 1, wherein said isomerizing comprises isomerizing at least one corresponding allylic substrate selected from the group consisting of 3,4-diacetoxy-1-butene, 1,4-diacetoxy-2-butene, and a mixture thereof, to produce at least one allylic isomer selected from the group consisting of 1,4-diacetoxy-2-butene, 3,4-diacetoxy-1-butene, and a mixture thereof.

29. The process according to claim 28, wherein said allylic substrate is obtained by a diacetoxylation of butadiene.

30. The process according to claim 29, further comprising separating a mixture comprising 50–100 mol % of 3,4-diacetoxy-1-butene and 0–50 mol % of 3-butene-1,2-diol monoacetoxylate from a reaction product obtained by said diacetoxylation; wherein said allylic substrate is comprised within said mixture.

31. The process according to claim 29, further comprising separating a mixture comprising 50–100 mol % of 1,4-diacetoxy-2-butene and 0–50 mol % of 1-acetoxy-4-hydroxy-2-butene from a reaction product obtained by said diacetoxylation; wherein said allylic substrate is comprised within said mixture.

32. The process according to claim 1, wherein said isomerizing is carried out in a reaction system, and wherein at least one compound (C) is present in said reaction system; and wherein said compound (C) is at least one selected from the group consisting of butane diol monoacetoxylate, 1-acetoxybutane-2-one, 4-acetoxybutanal, 4-acetoxycrotonaldehyde, diacetoxybutane, acetoxyhydroxybutane, butane diol, 1-acetoxy-1,3-butadiene, diacetoxyoctadiene, and mixtures thereof.

33. A process according to claim 32, wherein said compound (C) is present in a weight ratio ranging from 1:1 to 1:10000 based on the total weight of said allylic substrate.

34. The process according to claim 1, wherein said isomerizing is carried out in a reaction mixture, and wherein water is present in said reaction mixture in an amount of 0.1–5 wt. %, based on the total weight of said reaction mixture.

35. The process according to claim 1, wherein said isomerizing is carried out in a reaction system, and wherein acetic acid is present in said reaction system, and wherein water is present in a weight ratio of less than or equal to 1 based on the weight of said acetic acid.

36. The process according to claim 1, further comprising esterifying at least one selected from the group consisting of 3-butene-1,2-diol monoacetoxylate, 1-acetoxy-4-hydroxy-2-butene, and a mixture thereof to obtain at least one selected from the group consisting of, respectively, 3,4-diacetoxy-1-butene, 1,4-diacetoxy-2-butene, and a mixture thereof.

37. The process according to claim 36, wherein said esterifying is carried out in the presence of acetic anhydride.

38. The process according to claim 36, wherein said esterifying is carried out in the presence of an ion-exchange resin and acetic acid.

39. The process according to claim 36, wherein said esterifying comprises esterifying 3-butene-1,2-diol monoacetoxylate to obtain 3,4-diacetoxy-1-butene.

40. The process according to claim 39, wherein said esterifying is carried out in the presence of acetic anhydride, and wherein a molar ratio of said 3-butene-1,2-diol monoacetoxylate to said acetic anhydride ranges from 0.5 to 2.

41. The process according to claim 39, wherein said esterifying is carried out in the presence of an ion-exchange resin, and wherein a weight ratio of said 3-butene-1,2-diol monoacetoxylate to said ion-exchange resin ranges from greater than zero to 1.

42. The process according to claim 36, wherein said 3-butene-1,2-diol monoacctoxylate is at least one selected from the group consisting of 4-acetoxy-3-hydroxy-1-butene, 3-acetoxy-4-hydroxy-1-butene, and a mixture thereof.

43. The process according to claim 1, further comprising, prior to said isomerizing, esterifying at least one selected from the group consisting of 3-butene-1,2-diol monoacetoxylate, 1-acetoxy-4-hydroxy-2-butene, and a mixture thereof to obtain a reaction mixture comprising at least one selected from the group consisting of, respectively, 3,4-diacetoxy-1-butene, 1,4-diacetoxy-2-butene, and a mixture thereof; and wherein said allylic substrate is comprised within said reaction mixture.

44. The process according to claim 43, wherein said esterifying is carried out in the presence of acetic anhydride.

45. The process according to claim 43, wherein said esterifying is carried out in the presence of an ion-exchange resin and acetic acid.

46. The process according to claim 43, wherein said 3-butene-1,2-diol monoacetoxylate is at least one selected from the group consisting of 4-acetoxy-3-hydroxy-1-butene, 3-acetoxy-4-hydroxy-1-butene, and a mixture thereof.

47. The process according to claim 1, wherein said allylic isomer is obtained in a yield of 10% or more, and wherein said metal compound is not substantially deposited during said isomerizing.

48. The process according to claim 1, further comprising hydrogenating and hydrolyzing said corresponding allylic isomer to obtain a hydrogenation and hydrolysis product.

49. The process according to claim 48, wherein said corresponding allylic isomer is 1,4-diacetoxy-2-butene.

50. The process according to claim 48, wherein said hydrogenation and hydrolysis product is at least one selected from the group consisting of 1,4-butanediol, tetrahydrofuran, and a mixture thereof.

51. The process according to claim 50, further comprising producing a polyester or a polyurethane or both from said 1,4-butanediol.

52. The process according to claim 51, further comprising producing an engineering plastic or fiber or both from said polyurethane.

53. The process according to claim 52, further comprising producing a polyalkylene ether glycol from said tetrahydrofuran.

54. A process, comprising:
isomerizing a mixture comprising 3,4-diacetoxy-1-butene and 1,4-diacetoxy-2-butene to produce a mixture of corresponding allylic isomers comprising 1,4-diacetoxy-2-butene and 3,4-diacetoxy-1-butene, wherein said isomerizing is conducted in the presence of a catalyst comprising a Group VIII-X metal compound and a phosphite compound.

55. A process, comprising:
isomerizing 3,4-diacetoxy-1-butene to produce a corresponding allylic isomer, 1,4-diacetoxy-2-butene, wherein said isomerizing is conducted in the presence of a catalyst comprising a Group VIII-X metal compound and a phosphite compound.

56. A process, comprising:
isomerizing a mixture comprising 3,4-diacetoxy-1-butene and 3-butene-1,2-diolmonoacetoxylate to produce a mixture of corresponding allylic isomers comprising 1,4-diacetoxy-2-butene and 1-acetoxy-4-hydroxy-2-butene, wherein said isomerizing is conducted in the presence of a catalyst comprising a Group VIII-X metal compound and a phosphite compound.

57. A process, comprising:
isomerizing a mixture comprising 3,4-disubstituted-1-butene and 3-butene-1,2-diolmonosubstituted to produce a mixture of corresponding allylic isomers comprising 1,4-disubstituted-2-butene and 1-monosubstituted-4-hydroxy-2-butene, wherein said isomerizing is conducted in the presence of a catalyst comprising a Group VIII-X metal compound and a phosphite compound.

58. The process according to claim 1, said allylic substrate is comprised within a reaction mixture comprising at least one 3-butene-1,2-diol monoacetoxylate, and wherein said process further comprises esterifying, simultaneously with the isomerizing, at least one 3-butene-1,2-diol monoacetoxylate to obtain 3,4-diacetoxy-1-butene.

59. The process according to claim 58, wherein said esterifying is carried out in the presence of acetic anhydride.

60. The process according to claim 58, wherein said esterifying is carried out in the presence of an ion-exchange resin and acetic acid.

61. The process according to claim 58, wherein said esterifying is carried out in the presence of acetic anhydride, and wherein a molar ratio of said 3-butene-1,2-diol monoacetoxylate to said acetic anhydride ranges from 0.5 to 2.

62. The process according to claim 58, wherein said esterifying is carried out in the presence of an ion-exchange resin, and wherein a weight ratio of said 3-butene-1,2-diol monoacetoxylate to said ion-exchange resin ranges from greater than zero to 1.

63. The process according to claim 58, wherein said 3-butene-1,2-diol monoacetoxylate is at least one selected from the group consisting of 4-acetoxy-3-hydroxy-1-butene, 3-acetoxy-4-hydroxy-1-butene, and a mixture thereof.

64. The process according to claim 1, further comprising, prior to said isomerizing, esterifying at least one 3-butene-1,2-diol monoacetoxylate to obtain a reaction mixture comprising at least one 3,4-diacetoxy-1-butene and wherein said allylic substrate is comprised within said reaction mixture.

65. The process according to claim 64, wherein said esterifying is carried out in the presence of acetic anhydride.

66. The process according to claim 64, wherein said esterifying is carried out in the presence of an ion-exchange resin and acetic acid.

67. The process according to claim 64, wherein said 3-butene-1,2-diol monoacetoxylate is at least one selected from the group consisting of 4-acetoxy-3-hydroxy-1-butene and 3-acetoxy-4-hydroxy-1-butene.

* * * * *